United States Patent [19]
Hidaka et al.

[11] Patent Number: 5,972,976
[45] Date of Patent: Oct. 26, 1999

[54] AMINOSTILBAZOLE DERIVATIVE AND MEDICINE

[75] Inventors: Hiroyoshi Hidaka, Nagoya; Akira Matsuura, Shiga; Masato Matsuda, Otsu, all of Japan

[73] Assignee: Nippon Shinyaku Company, Limited

[21] Appl. No.: 08/765,131

[22] PCT Filed: Apr. 5, 1995

[86] PCT No.: PCT/JP95/00658

§ 371 Date: Oct. 2, 1996

§ 102(e) Date: Oct. 2, 1996

[87] PCT Pub. No.: WO95/27699

PCT Pub. Date: Oct. 19, 1995

[30] Foreign Application Priority Data

Apr. 6, 1994 [JP] Japan ..................................... 6-068252

[51] Int. Cl.$^6$ ...................... C07D 413/00; C07D 241/02; C07D 213/36; C07D 211/72
[52] U.S. Cl. ................... 514/357; 514/235.8; 514/236.2; 514/236.5; 514/237.2; 514/252; 514/255; 514/256; 514/332; 514/352; 544/120; 544/122; 544/124; 544/238; 544/295; 544/357; 546/264; 546/255; 546/304; 546/329; 546/338
[58] Field of Search ............................. 514/235.8, 236.2, 514/236.5, 237.2, 252, 255, 256, 332, 352, 351; 544/120, 122, 124, 238, 295, 357; 546/264, 255, 304, 329, 338

[56] References Cited

U.S. PATENT DOCUMENTS 5,534,654  7/1996  Ohtani et al. .............................. 564/90

FOREIGN PATENT DOCUMENTS 0472053  2/1992  European Pat. Off. .

OTHER PUBLICATIONS

Chemical Abstracts 106:6405, abstract of EP 176473, 1986.
Chemical Abstracts 106:6404, abstract of EP 176474, 1986.
J. Med. Chem. 1991, 34, 2579–2588.
J. Med. Chem. 1994, 37, 151–157.
Eur. J. Med. Chem. 1985, 20, 487–491.

*Primary Examiner*—D. Margaret M. Mach
*Attorney, Agent, or Firm*—Graham & James LLP

[57] ABSTRACT

The invention relates to an aminostilbazole derivative of the following formula or a hydrate thereof, and a salt thereof.

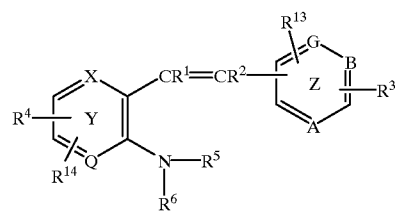

wherein $R^1$ and $R^2$ each represents hydrogen etc.; $R^3$, $R^4$, $R^{13}$, and $R^{14}$ each represents hydrogen, $C_{1-3}$ acyl, halogen, hydroxy etc.; $R^5$ represents hydrogen or hydroxy-substituted $C_{1-3}$ alkyl etc.; $R^6$ represents benzenesulfonyl substituted by $C_{1-3}$ alkoxy etc.; ring Y represents phenyl etc.; ring Z represents 4-pyridyl, its oxide etc. The compound is useful or the treatment of various malignant tumors.

21 Claims, No Drawings

AMINOSTILBAZOLE DERIVATIVE AND MEDICINE

This application is a 371 of PCT/JP95/00,658, filed Apr. 5, 1995.

TECHNICAL FIELD

The present invention relates to a medicinally useful, novel aminostilbazole derivative or its hydrate and a pharmaceutically acceptable salt thereof.

BACKGROUND TECHNOLOGY

In cancer chemotherapy today, a variety of anticancer drugs such as alkylating agents, topoisomerase inhibitors, antimetabolites, cytoskeletal system inhibitors, enzymes, hormones, antihormones, antibiotics, and plant products are being employed.

Referring to anticancer hormones, particularly stilbenes having a nuclear skeletal structure resembling that of the compound of the present invention, stilbestrol phosphate and tamoxifen and so on have been used in the treatment of cancer of the prostate, breast and other tissues but they are not fully satisfactory from the standpoint of efficacy and in view of the adverse effects associated with their hormonal activity.

Antimicrotubule agents or tubulin agonists have potent anticancer activity with a broad anticancer spectrum and constitute a clinically important class of drugs.

The inhibition of tubulin polymerization is attracting attention of late as a mechanism of action of anticancer agents. The microtubule is an ubiquitous intracellular structure and, as a major component of the mitotic spindle, plays an important role in cell division. An antimicrotubule agent binds to the tublin protein of the microtubule and disrupts the dynamics of the microtubule by orienting it either in the direction of assembly or in that of disassembly, thus manifesting its anticancer activity. Vinca alkaloids, which are of plant origin, are known as representative tubulin polymerization-inhibitory anticancer agents and recently taxols are gathering attention because of their potent anticancer efficacy associated with promotion of tubulin polymerization. Being derived from plants, these compounds have availability problems. Such anticancer drugs acting on microtubules are available as injections which cannot be conveniently used and, because of their side effects, are not being used in multiple-dose regimens. Quite recently, the low molecular weight substance E7010 (Cancer and Chemotherapy, 1993 20: 34–41, JP Kokai H5-39256) has been discovered and clinical trials with the compound are now being watched by many with much interest.

It is reported that stilbene derivatives represented by (Z)-3,4,5-trimethoxy-4'-methoxystilbene as well as dihydrostilbene derivatives, which have a stilbene nucleus similar to that of the compound of the present invention, have tubulin polymerization-inhibitory activity (J. Med. Chem. 1991, 34, 2579).

Meanwhile, it is reported that hydroxamic acid derivatives substituted by a phenylethenyl-heterocyclic group show antiallergic activity (Eur. J. Med. Chem. 1985, 20, 487–491). There also is a report on the interaction between tetrahydrostilbazole and monoamine oxidase (J. Med. Chem. 1994, 37, 151–157).

DISCLOSURE OF INVENTION

The present invention has for its object to provide a novel compound which shows an excellent anticancer action without eliciting those adverse reactions which are experienced with the anticancer hormones available today and can be administered by the oral route.

To accomplish the above object, the inventors of the present invention have synthesized a variety of compounds and evaluated them. In the course of the research endeavor, they have found that the compound of the following general formula [I] has very potent anticancer activity with low toxicity and has perfected the present invention.

The present invention relates to a compound of the following general formula [I], its salt, and an anticancer composition comprising said compound or salt as an active ingredient.

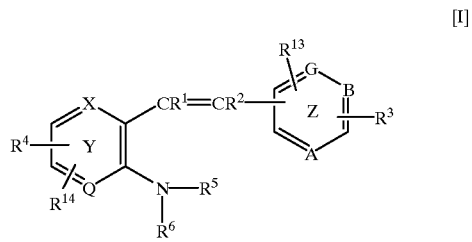

[I]

wherein $R^1$ and $R^2$ are the same or different and each represents hydrogen, alkyl of 1–6 carbon atoms, acyl of 1–6 carbon atoms, cyano, or —COOR (R represents hydrogen or $C_{1-6}$ alkyl).

$R^3$, $R^4$, $R^{13}$, and $R^{14}$ are the same or different and each represents hydrogen, alkyl of 1–6 carbon atoms, alkoxy of 1–6 carbon atoms, haloalkoxy of 1–6 carbon atoms, acyl of 1–6 carbon atoms, acyloxy of 1–6 carbon atoms, hydroxy, halogen, nitro, cyano, amino, acylamino of 1–6 carbon atoms, aminoalkyloxy of 1–6 carbon atoms, or morpholinoalkyloxy with 1–6 carbon atoms in the alkyl moiety. $R^3$ and $R^{13}$ or $R^4$ and $R^{14}$ may jointly represent methylenedioxy.

$R^5$ represents (1) hydrogen, (2) alkyl of 1–6 carbon atoms which is optionally substituted by halogen, amino, monoalkylamino of 1–6 carbon atoms, dialkylamino of 1–6 carbon atoms, morpholino, alkoxy of 1–6 carbon atoms, or hydroxy, (3) alkenyl of 2–6 carbon atoms which is optionally substituted by halogen, (4) alkynyl of 2–6 carbon atoms, or (5) acyl of 1–6 carbon atoms.

$R^6$ represents (1) aroyl of 7–11 carbon atoms which is optionally substituted by alkyl of 1–6 carbon atoms, alkoxy of 1–6 carbon atoms, or halogen or (2) arylsulfonyl of 6–10 carbon atoms which is optionally substituted by alkyl of 1–6 carbon atoms, alkoxy of 1–6 carbon atoms, haloalkoxy of 1–6 carbon atoms, hydroxy, nitro, or halogen.

A, B, G, Q, and X may be the same or different and each represents N, CH, N→O, or $N^+$—$(R^7)E^-$ ($R^7$ represents alkyl of 1–6 carbon atoms or arylalkyl of 7–14 carbon atoms; $E^-$ represents an anion such as halogen ion, chlorate ion, or nitrate ion). Excluded is the case in which A, B, and G concurrently represent N and the case in which A, B, G, Q, and X concurrently represent CH.

Y and Z are tentative designations of the corresponding rings.

The present invention is characterized by the very structure of the compound of the general formula [I]. The structural feature of the compound of the invention resides in the substitution of the ortho-position of phenyl in the stilbazole nucleus with an amino group.

The compound having the above structural feature is not only a novel compound never documented heretofore but also a compound having the beneficial pharmacologic properties to be mentioned hereinafter with a low toxic potential.

The present invention is now described in detail.

In the context of the present invention, alkyl means a straight-chain or branched-chain alkyl groups of 1–6 carbon atoms, thus including methyl, ethyl, n-propyl, isopropyl, n-butyl, isobutyl, sec-butyl, tert-butyl, n-pentvl, isopentyl, n-hexyl, and isohexyl, among others. Particularly preferred is alkyl of 1–3 carbon atoms. The alkoxy includes straight-chain or branched-chain alkoxy groups of 1–6 carbon atoms, such as methoxy, ethoxy, n-propoxy, isopropoxy, n-butoxy, isobutoxy, sec-butoxy, tert-butoxy, n-pentyloxy, isopentyloxy, n-hexyloxy, and isohexyloxy, among others. Particularly preferred is alkoxy of 1–3 carbon atoms. The alkenyl means any of straight-chain or branched-chain alkenyl groups of 2–6 carbon atoms, thus including vinyl, 1-propenyl, 2-propenyl, isopropenyl, 2-butenyl, 3-butenyl, isobutenyl, methalyl, prenyl, isoprenyl, and 1,1-dimethylallyl, among others. Particularly preferred is alkenyl of 2–4 carbon atoms. The alkynyl includes straight-chain or branched-chain alkynyl groups of 2–6 carbon atoms, such as ethynyl, 1-propynyl, 2-propynyl, 2-butynyl, 3-butynyl, and 3-methyl-2-butynyl, among others. In particular, alkynyl of 2–4 carbon atoms is preferred. The acyl includes straight-chain or branched-chain alkanoyl of 1–6 carbon atoms, such as formyl, acetyl, propionyl, butyryl, isobutyryl, valeryl, isovaleryl, and pivaloyl, among others. The acyl may be substituted by halogen as it is the case with trifluoroacetyl. In particular, acyl of 2–4 carbon atoms is preferred. The aroyl includes groups of 7–11 carbon atoms, such as benzoyl, α-naphthoyl, and β-naphthoyl, among others. Benzoyl is particularly preferred. The aryl of said arylsulfonyl includes groups of 6–10 carbon atoms, such as phenyl, α-naphthyl, and β-naphthyl, to mention just a few examples. In particular, phenyl is preferred. The aryl of said aroyl or arylsulfonyl may be substituted by at least one, and either the same or different, substituent groups such as those mentioned in the definition of $R^6$. The halogen includes chlorine, fluorine, bromine and iodine.

Ring Y includes phenyl, 2-pyridyl, 3-pyridyl, 4-pyridyl, and pyrazinyl, among others. Preferred is phenyl and, in particular, unsubstituted phenyl or ortho-substituted phenyl. Ring Z includes phenyl, 2-pyridyl, 3-pyridyl, 4-pyridyl, pyrazinyl, 2-pyrimidinyl, 4-pyrimidinyl, 5-pyrimidinyl, 3-pyridazinyl, and 4-pyridazinyl, among others. Preferred is pyridyl and, in particular, 4-pyridyl. Above all else, unsubstituted or 3-substituted 4-pyridyl is preferred.

Preferred are compounds such that, in general formula [I], $R^1$, $R^2$, $R^3$, $R^4$, $R^{13}$, and $R^{14}$ are all hydrogen, —$NR^5R^6$ is 4-[(methoxyphenyl)sulfonyl]amino or N-(hydroxyethyl)-N-[(4-methoxyphenyl)sulfonyl]amino, ring Y is unsubstituted phenyl or hydroxy- or methoxy-substituted phenyl, and ring Z is either unsubstituted 4-pyridyl or 4-pyridyl substituted by hydroxy, acetyloxy or fluorine, or the N-oxide thereof.

The salt of compound [I] which falls within the scope of the invention includes salts with inorganic acids such as hydrochloric acid, sulfuric acid, nitric acid, phosphoric acid, hydrofluoric acid, hydrobromic acid, etc. and salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid, among other acids. Where $R^1$ or $R^2$ is COOH, the corresponding salt includes salts with alkali metals or alkaline earth metals such as sodium, potassium, calcium, etc.

The compound of the present invention may exist in cis(Z) and trans(E) forms. These respective isomers and their mixtures also fall within the scope of the present invention.

In addition to the specific compounds synthesized in the production examples which are presented hereinafter, the compound of the present invention includes the following specific compounds, among others.

4-[1-Cyano-2-[2-[[(p-methoxyphenyl)sulfonyl]amino]phenyl]ethenyl]pyridine,

4-[1,2-Dimethyl-2-[2-[[(p-methoxyphenyl)sulfonyl]amino]phenyl]ethenyl]pyridine,

4-[1-Methoxycarbonyl-2-[2-[[(p-methoxyphenyl)sulfonyl]amino]phenyl]ethenyl]pyridine, 2-Chloro-4-[2-[2-[[(p-methoxyphenyl)sulfonyl]amino]phenyl]ethenyl]pyridine, 2-Methoxy-4-[2-[2-[[(p-methoxyphenyl)sulfonyl]amino]phenyl]ethenyl]pyridine, 3-Methoxy-4-[2-[2-[[(p-methoxyphenyl)sulfonyl]amino]phenyl]ethenyl]pyridine, 4-[2-[2-[[[(p-Methoxyphenyl)sulfonyl]amino]-5-methoyl]phenyl]ethenyl]pyridine, 4-[2-[[2-[[(p-Methoxyphenyl)sulfonyl]amino]-5-methoxy]phenyl]ethenyl]pyridine, 4-[2-[2-[[(2,4-Dimethoxyphenyl)sulfonyl]amino]-5-methoxyphenyl]ethenyl]pyridine, 4-[2-[2-[[(2,4,6-Trimethoxyphenyl)sulfonyl]amino]-5-methoxyphenyl]ethenyl]pyridine, 4-[2-[[2-[[(3,4,5-Trimethoxyphenyl)sulfonyl]amino]-5-methoxy]phenyl]ethenyl]pyridine, 4-[2-Cyano-2-[2-[[(p-methoxyphenyl)sulfonyl]amino]-5-methoxyphenyl]ethenyl]pyridine, 4-[2-[2-[(p-Methoxybenzoyl)amino]phenyl]ethenyl]pyridine, 2-Fluoro-4-[2-[2-[[(p-methoxyphenyl)sulfonyl]amino]phenyl]ethenyl]pyridine 1-oxide, 4-[2-[2-[N-Propionyl-N-[(p-methoxyphenyl)sulfonyl]amino]phenyl]ethenyl]pyridine 1-oxide, 4-[2-[2-[N-Formyl-N-[(p-methoxyphenyl)sulfonyl]amino]phenyl]ethenyl]pyridine 1-oxide, 4-[2-[2-(N-Butyryl-N-[(p-methoxyphenyl)sulfonyl]amino]phenyl]ethenyl]pyridine 1-oxide, 3-Fluoro-4-[2-[2-[[(p-methoxyphenyl)sulfonyl]amino]phenyl]ethenyl]pyridine, 2-Fluoro-4-[2-[2-[[(p-methoxyphenyl)sulfonyl]amino]phenyl]ethenyl]pyridine, 4-[2-[2-[N-Acetyl-N-[(p-methoxyphenyl)sulfonyl]amino]phenyl]ethenyl]pyridine, 2-Methoxy-4-[2-[2-[[(p-methoxyphenyl)sulfonyl]amino]phenyl]ethenyl]pyridine 1-oxide.

Among species of the compound of the present invention, (E)-4-[2-[2-[[(p-methoxyphenyl)sulfonyl]amino]phenyl]ethenyl]pyridine and its hydrochloride (compound of Example 3), (E)-4-[2-[2-[[(p-methoxyphenyl)sulfonyl]amino]phenyl]ethenyl]pyridine 1-oxide (compound of Example 20), (E)-4-[2-[2-[N-(2-hydroxyethyl)-N-[(p-methoxyphenyl)sulfonyl]amino]phenyl]ethenyl]pyridine 1-oxide (compound of Example 49), (E)-4-[2-[2-[N-(2-hydroxyethyl)-N-[(p-methoxyphenyl)-sulfonyl]amino]phenyl]ethenyl]pyridine (compound of Example 34), and (E)-4-[2-[2-[N-acetyl-N-[(p-methoxyphenyl)sulfonyl]amino]phenyl]ethenyl]pyridine 1-oxide (compound of Example 57) are preferred. Particularly preferred are compounds of Example 3, Example 34, and Example 49.

The compound of the present invention can be produced typically by the following processes.

Process 1

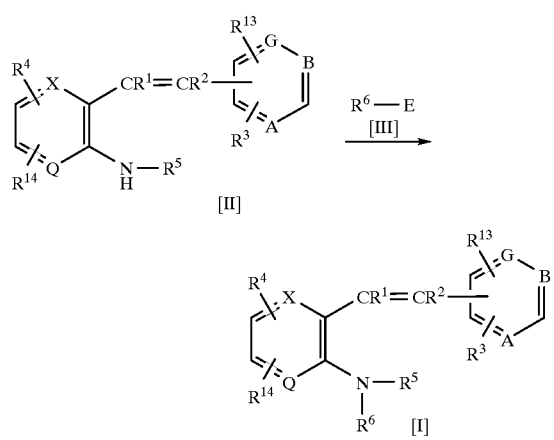

(In the above reaction schema, $R^1$, $R^2$, $R^3$, $R^4$, $R^5$, $R^6$, $R^{13}$, $R^{14}$, A, B, G, Q, and X have the meanings defined hereinbefore. E represents hydroxy or a leaving group)

The leaving group includes but is not limited to chloro, bromo, sulfoxy, imidazolyl, and carboxy.

An amine of general formula [II] is reacted with either a carboxylic acid or a reactive derivative (E=leaving group) of a carboxylic acid or sulfonic acid, which has the general formula [III], in a suitable solvent to give [I]. The reaction solvent may be any kind of solvent that does not interfere with the reaction, thus including ethers such as tetrahydrofuran, dioxane and diethyl ether; hydrocarbons such as benzene and toluene; halogenated hydrocarbons such as methylene chloride and chloroform; ketones such as acetone and methyl ethyl ketone; aprotic solvents such as N,N-dimethylformamide, N,N-dimethylacetamide, pyridine and acetonitrile, and various mixtures of such solvents. The reactive derivative of a sulfonic or carboxylic acid that can be used includes those kinds of reactive derivatives which are conventionally used, such as the sulfonyl halide, carboxyl halide, sulfonic anhydride, carboxic anhydride, N-sulfonyl imidazolide, activated amide and activated ester. Above all else, the sulfonyl halide and carboxyl halide are preferred. Such acid halide includes acid chloride and acid bromide. The acid anhydride includes the mixed anhydrides prepared from monoalkylcarbonic acids and mixed anhydrides prepared from aliphatic carboxylic acids (e.g. acetic acid, pivalic acid, valeric acid, isovaleric acid, trifluoroacetic acid, etc.), as well the symmetric anhydride. The activated amide includes such acid amides as imidazole, pyrazole, 4-substituted imidazole, dimethylpyrazole, triazole, tetrazole, and benzothiazole, among others. The activated ester includes such esters as the methyl ester, methoxymethyl ester, propargyl ester, 4-nitrophenyl ester, 2,4-dinitrophenyl ester, trichlorophenyl ester, methanesulfonyl ester, and ester derivatives such as N-hydroxysuccinimide and N-hydroxyphthalimide, among others.

When a sulfonic acid halide or a carboxylic acid halide is used for this reaction, the reaction is preferably conducted in the presence of a suitable acid removing agent. The acid removing agent that can be used includes alkali metal compounds such as sodium hydrogen carbonate, potassium carbonate, sodium hydroxide, potassium hydroxide, sodium hydride and sodium methoxide, and organic tertiary amines such as triethylamine and triethylenediamine, For instance. It is preferable to use a basic solvent such as pyridine as the reaction solvent, for then the acid removing agent need not be employed. This reaction proceeds at room temperature in many instances but where necessary the reaction can be carried out under cooling or heating, typically in the range of −78° C. to 150° C. or preferably 0° C. to 120° C. The proportion of compound [III] based on amine [II] is preferably 1 through 10 molar equivalents and, for still better results, 1 through 3 molar equivalents when the acid removing agent is employed. When the acid removing agent is not used, the proportion of [III] is less than equimolar and preferably in the range of 0.5 through 0.1 molar equivalent. The reaction time, which depends on species of starting compounds and species of solvent used, reaction temperature, etc., is generally 5 minutes through 70 hours. Compound [Ia] ($R^6$ in formula [I] is aroyl) can also be produced by reacting an amine [II] with a carboxylic acid in the presence of a condensing agent such as N,N'-dicyclohexylcarbodiimide (DCC), carbonyldiimidazole or diphenylphosphoryl azide (DPPA).

The compound of the present invention can also be produced by the following processes.

Process 2

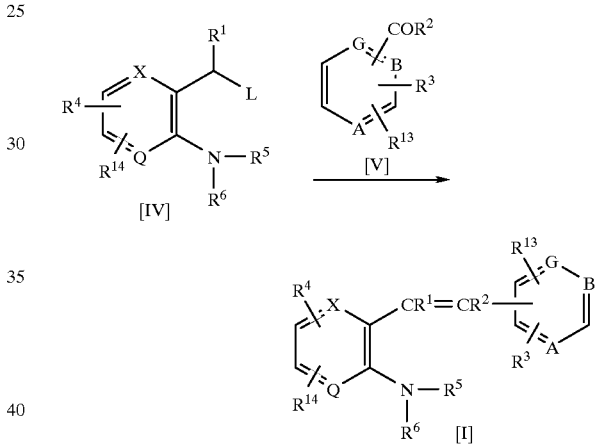

(In the above reaction schema, A, B, G, Q, X, $R^1$ $R^2$, $R^3$, $R^4$, $R^5$, $R^6$, $R^{13}$, and $R^{14}$ have the meanings defined hereinbefore. L represents a leaving group such as —P(Ph)$_3$Br or —PO(OR$^0$)$_2$ (R$^0$ represents alkyl)]

Thus, the compound of general formula [I] can be produced by reacting a phosphonium salt or alkylphosphorous acid diester of general formula [IV] with a ketone or aldehyde of general formula [V] by the per se known procedure (Org. React., 14, 270) or any version thereof.

Process 3

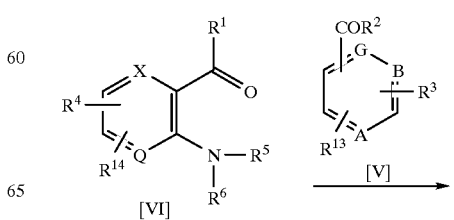

-continued

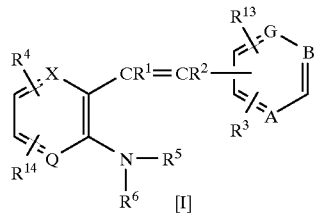

(In the above reaction schema, A, B, G, Q, X, $R^1$ $R^2$, $R^3$, $R^4$, $R^5$, $R^6$, $R^{13}$, and $R^{14}$ have the meanings defined hereinbefore)

Thus, compound [VI] is reacted with compound [V] in a suitable solvent to give compound [I]. This reaction can be conducted generally in accordance with the known process (J. Org. Chem. 41, 392). Thus, compound [I] can be produced by reacting compound [V] with compound [VI] in the presence of the low-valence titanium generated by using titanium trichloride or titanium tetrachloride in combination with a reducing substance such as lithium, potassium, n-butyllithium, lithium aluminum hydride or zinc.

Process 4

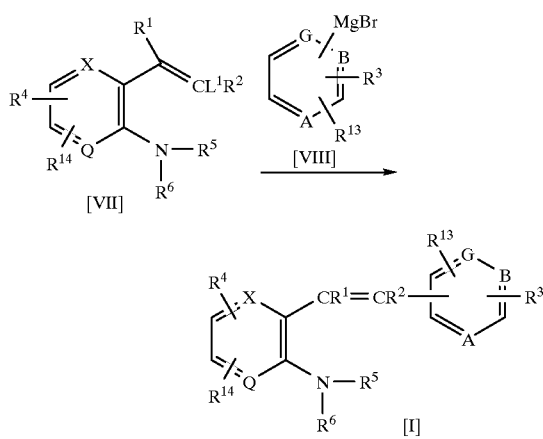

(In the above reaction schema, A, B, G, Q, X, $R^1$ $R^2$, $R^3$, $R^4$, $R^5$, $R^6$, $R^{13}$, and $R^{14}$ have the meanings defined hereinbefore. $L^1$ represents halogen such as iodine)

Thus, compound [I] can be produced by reacting compound [VII] with a Grignard reagent [VIII] generally in accordance with the known process (Tetrahedron Letters, 30, 403). Thus, these compounds are reacted in a solvent inert to the reaction in the presence of a complex compound of a metal such as nickel (Ni) or palladium (Pd) at −78° C. to 100° C. and preferably 0° C. to 70° C. The solvent that can be used includes ethers such as anhydrous diethyl ether and tetrahydrofuran, and aromatic hydrocarbons such as benzene and toluene. Compound [VII] is used generally in a proportion of 1.0–0.8 equivalents based on Grignard reagent [VIII].

Process 5

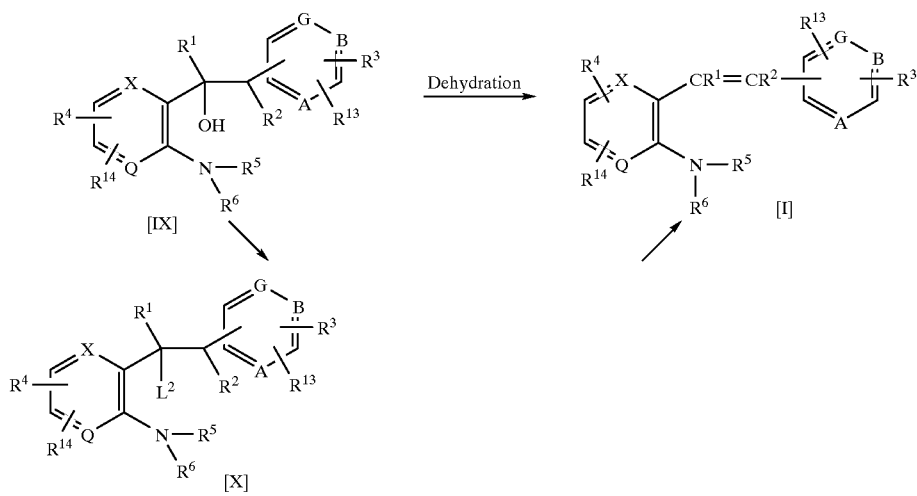

(In the above reaction schema, A, B, G, Q, X, $R^1$, $R^2$, $R^3$, $R^4$, $R^5$, $R^6$, $R^{13}$, and $R^{14}$ have the meanings defined hereinbefore. $L^2$ represents a leaving group such as chloro, bromo, acetoxy, etc.)

Compound [I] can be produced by heating compound [IX] together with a mineral acid such as sulfuric acid or phosphoric acid, an organic acid such as oxalic acid or p-toluenesulfonic acid, a Lewis acid such as boron trifluoride, or a base such as potassium hydrogen sulfate. Compound [I] can also be produced by treating compound [IX] with a halogenating reagent, a sulfonating agent or an esterifying agent to give a reactive derivative [X] and then subjecting [X] to reaction under basic conditions in the same manner as Process 1.

Process 6

(applicable when $R^1=R^2=H$ in formula [I], exclusive of the case in which $R^3$, $R^4$, $R^{13}$ or $R^{14}$ is nitro or cyano and the case in which $R^5$ is alkenyl, alkynyl or acyl)

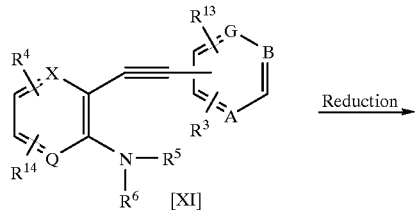

Reduction

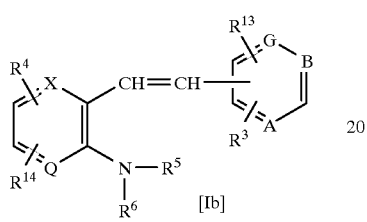

(In the above reaction schema, A, B, G, Q, X, $R^3$, $R^4$, $R^5$, $R^6$, $R^{13}$, and $R^{14}$ have the meanings defined hereinbefore)

Compound [Ib] (compound of formula [I] wherein each of $R^1$ and $R^2$ is hydrogen) can be produced by subjecting compound [XI] to reduction with lithium aluminum hydride or catalytic reduction.

Process 7

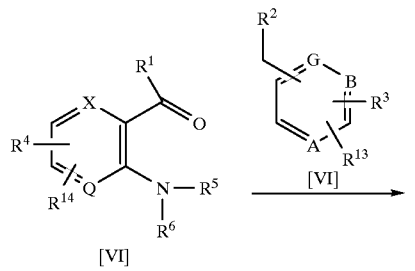

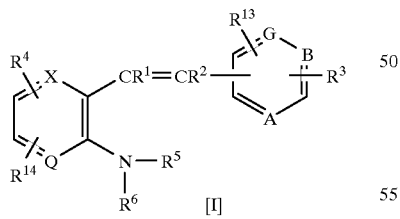

(In the above reaction schema, A, B, G, Q, X, $R^1$, $R^2$, $R^3$, $R^4$, $R^5$, $R^6$, $R^{13}$, and $R^{14}$ have the meanings defined hereinbefore)

Thus, compound [I] can be produced by subjecting compound [VI] and compound [XII] to condensation reaction (as described in JP Kokai H5-506857, J. Med. Chem., 1994, 37, 151).

Process 8

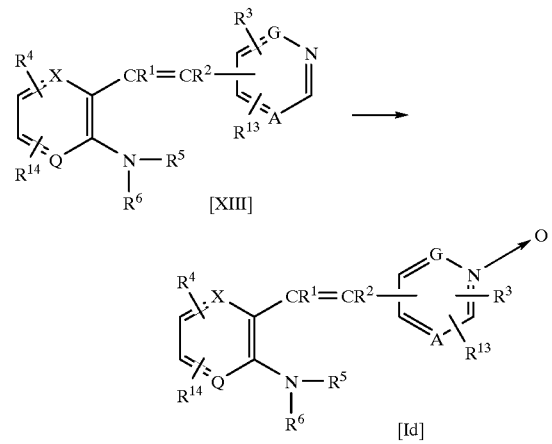

(In the above reaction schema, A, G, Q, X, $R^1$, $R^2$, $R^3$, $R^4$, $R^5$, $R^6$, $R^{13}$, and $R^{14}$ have the meanings defined hereinbefore).

Compound [Id] (comoound of formula [I] wherein B is N→O) can be produced by reacting compound [XIII] with an organic peroxide in accordance with the known procedure [Jikken Kagaku Koza (Experimental Chemistry Series) 21, Yukikagobutsu-no-Gosei (Synthesis of Organic Compounds) III (Part 2), p. 295, 1958).

Process 9

(exclusive of the case in which $R^5$ in general formula [I] is hydrogen)

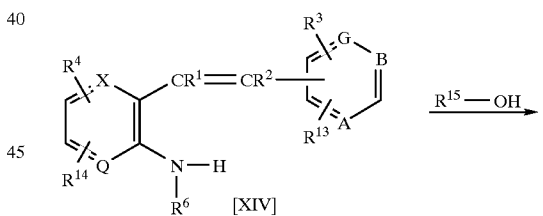

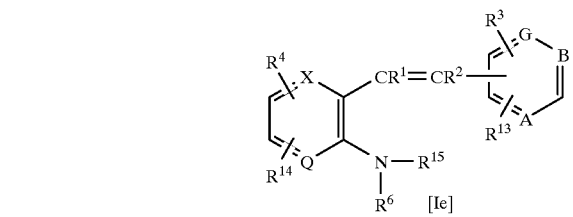

(In the above reaction schema, A, B, G, Q, X, $R^1$, $R^2$, $R^3$, $R^4$, $R^6$, $R^{13}$, and $R^{14}$ have the meanings defined hereinbefore. $R^{15}$ means any member other than hydrogen in the definition of $R^5$)

Thus, compound [Ie] (compound of formula [I] wherein $R^5$ is other than hydrogen) can be prepared by treating [XIV] with an alcohol of the formula $R^{15}$—OH (cf. Synthesis 1981, 1).

Process 10
(exclusive of the case in which $R^5$ in formula [I] is hydrogen)

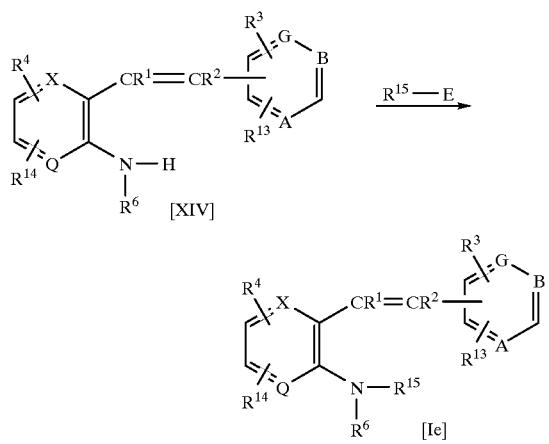

(In the above reaction schema, A, B, G, Q, X, $R^1$, $R^2$, $R^3$, $R^4$, $R^6$, $R^{13}$, $R^{14}$ and $R^{15}$ have the meanings defined hereinbefore. E represents a leaving group)

The leaving group includes chloro, bromo, iodo, carboxy, etc. [Ie] is produced by reacting a compound of general formula [XIV] with a compound of formula $R^{15}$—E in a suitable solvent. This reaction can be conducted essentially in the same manner as Process 1.

When the compound produced by any of the above processes is a carboxylic acid alkyl ester ($R^1$ or $R^2$ is COOR where R is alkyl), it can be subjected, if desired, to alkaline hydrolysis to give the free carboxylic (R=H) compound. This hydrolysis reaction can be carried out by stirring the ester compound in 1–5% potassium hydroxide or sodium hydroxide/aqueous alcohol (methanol, ethanol, propanol, or butanol) of 2–30 times as much by volume (preferably 5–10 times as much by volume) at room temperature to 100° C., preferably at the boiling temperature of the solvent used.

Alternatively, the hydrolysis reaction can be conducted using a large excess, preferably 10–20 times as much by volume, of an acid (e.g. fuming sulfuric acid, sulfuric acid, hydrochloric acid, hydrobromic acid, hydrobromic acid/acetic acid, chlorosulfonic acid, polyphosphoric acid, etc.) as the solvent at room temperature to 110° C.

The ester can be converted to a different ester by stirring it in 10–100 times as much by volume of the alcohol corresponding to the desired ester in the presence of a catalyst amount of concentrated sulfuric acid at 0° C. to 150° C., preferably at room temperature to 110° C.

When the product compound is a carboxylic acid ($R^1$ or $R^2$ is COOR wherein R is hydrogen), it can be esterified, if desired, to provide an ester ($R^1$ or $R^2$ is COOR where R is alkyl). This esterification reaction can be carried out by the per se known esterification methods, for example using thionyl chloride and an alcohol, an alcohol and a condensing agent (e.g. dicyclohexylcarbodiimide), or an alkyl halide or substituted alkyl halide and an alcoholate. Moreover, the carboxylic acid can be converted to a pharmacologically acceptable salt (e.g. salts with sodium, potassium, calcium, etc.) by the per se known procedure.

When the functional group or groups, e.g. amino, hydroxy, and carboxy, of the compound obtained by any of the above-mentioned processes have been protected, the protective group or groups can be eliminated by the per se known method such as acid treatment, alkali treatment, catalytic reduction, etc.

The above-mentioned base and hydrate can be produced by the per se known methods.

The resulting compound [I] thus produced can be isolated and purified by the per se known procedures such as concentration, pH adjustment, redistribution, solvent extraction, crystallization, recrystallization, fractional distillation, and chromatography.

The starting compound [II] can be produced in accordance with the known method (Eur. J. Med. Chem., 20, 487, 1985; J. Med. Chem., 37, 151, 1994.). By this method, the E-compound is mainly obtained. A mixture of the E- and Z-compounds can be produced by a known process (Org. React. 14, 270). The Z-compound can be produced by converting the triple-bond compound to the double-bond compound by catalytic reduction in the same manner as Process 6 described above.

The starting compound [IV] can be produced by the known method (Org. React. 14, 270) or a version thereof.

The starting compound [VI] can be produced in accordance with a known process (JP Kokai H4-330057).

The starting compound [VII] can be produced in accordance with a known process (Synthesis 1988, 236).

The starting compound [X] can be synthesized in accordance with a known process (Org. Syn. III, 200).

The starting compound [XII] can be synthesized by a known process (J. Org. Chem., 31, 4071).

For administration of the compound of the invention as a medicine, either the compound as it is or a pharmaceutical composition containing it in a medicinally acceptable, nontoxic, inert carrier at a concentration of, for example, 0.1% to 99.5%, preferably 0.5% to 90% is administered to mammals inclusive of humans.

The carrier that can be used includes solid, semisolid, or liquid diluents, fillers, and other formulation auxiliaries and at least one of them is selectively employed. The pharmaceutical composition is preferably administered in a unit dosage form. The pharmaceutical composition of the present invention can be administered by the oral route, parenterally (into tissues), locally (e.g. transdermally) or rectally. Of course, a dosage form suited for each route of administration should be used. Oral administration, for instance, is particularly preferred.

The dosage of the compound as an anticancer drug should preferably be adjusted in consideration of the patient's factors such as age, body weight, etc., nature and severity of disease, etc. as well as the route of administration but the usual oral dosage, as the active ingredient of the invention, for an adult patient is 0.1 mg to 500 mg daily or preferably 1 mg to 200 mg daily. A lower dosage may be sufficient in some cases, while a higher dosage beyond the above range may be needed in other cases. The above-mentioned daily dosage is preferably administered in 1–3 divided doses.

Oral administration can be carried out using a solid or liquid unit dosage form, such as bulk powders, powders, tablets, dragees, capsules, granules, suspensions, solutions, syrups, drops, sublingual tablets, and other forms.

Bulk powders are prepared by comminuting the active substance to a suitable particle size. Powders are prepared by comminuting the active substance to a suitable size and blending the resulting powder with similarly comminuted pharmaceutical carriers such as edible carbohydrates, e.g. starch, mannitol, etc., and other substances. Where necessary, flavorants, preservatives, dispersing agents, colorants, perfumes, etc. can be added.

Capsules are manufactured by granulating comminuted bulk particles, powders, or granules obtained in the manner described below for tablets and filling them in gelatin or other cadsule shells. Prior to filling, a lubricant or fluidizing agent, e.g. colloidal silica, talc, magnesium stearate, calcium stearate, solid polyethylene glycol, etc., can be added to the powders or granules. Moreover, the efficacy of the drug after ingestion of capsules may be improved by adding a disintegrator or a solubilizer, e.g. carboxymethylcellulose, carboxvmethylcellulose calcium, low-substitution-degree hydroxypropylcellulose, croscarmellose sodium, carboxystarch sodium, calcium carbonate, and sodium carbonate, among others.

The finely pulverized powder may be suspended and dispersed in vegetable oil, polyethylene glycol, glycerin or a surfactant and packaged in gelatin sheet to provide soft capsules. Tablets can be manufactured by preparing a powdery composition, granulating or slugging it, adding a disintegrator or a lubricant thereto, and compressing the mixture. The powdery composition can be prepared by mixing a properly comminuted substance with said diluent or base and may be supplemented, where necessary, with a binder (e.g. carboxymethylcellulose sodium, hydroxypropylcellulose, methylcellulose, hydroxypropylmethylcellulose, gelatin, polyvinylpyrrolidone, polyvinyl alcohol, etc.), a dissolution retardant (e.g. paraffin, wax, hydrogenated castor oil, etc.), a reabsorption promoter (e.g. quartenary salts), and an adsorbent (e.g. bentonite, kaolin, dicalcium phosphate, etc.). The powdery composition can be granulated by wetting the material with a binder, e.g. a syrup, a starch paste, a solution of gum arabic or cellulose, or a polymer solution and, then, passing the wet mass through a sieve by force. Instead of granulating the powder, it is possible to compress it using a tablet machine and crushing the resulting slugs, which are crude in form, into granules.

The granules thus obtained can be protected against inter-adhesion by adding a lubricant such as stearic acid, a salt of stearic acid, talc or mineral oil. The lubricated granules are then compressed into finished tablets.

The resulting bare tablets can be film-coated or sugar-coated.

Without being subjected to the above granulation or slugging step, the drug may be first admixed with a free-flowing inert carrier and directly compressed. A transparent or translucent protective coat comprising a hermetic shellac film, a sugar or polymer coat, or a wax glaze coat can also be applied.

Other oral dosage forms such as solutions, syrups, elixirs, etc. can also be provided in unit dosage forms each containing a predetermined amount of the drug. A syrup can be manufactured by dissolving the compound in a suitable pleasantly flavored aqueous vehicle, while an elixir can be manufactured using a nontoxic alcoholic vehicle. A suspension can be prepared by dispersing the compound in a nontoxic vehicle. Where necessary, solubilizers and emulsifiers (e.g. ethoxylated isostearyl alcohol, polyoxyethylenesorbitol esters, etc.), preservatives, flavorants (e.g. peppermint oil, saccharin, etc.) can also be added.

Where necessary, a unit dose formulation for oral administration may be microencapsulated. This formulation can also be coated with, or embedded in, a polymer, a wax, or the like to provide a prolonged action or sustained release DDS.

Parenteral administration can be made using a liquid unit dosage form, such as a solution or a suspension, for subcutaneous, intramuscular or intravenous administration. Such a unit dosage form can be manufactured by suspending or dissolving a predetermined amount of the compound in a nontoxic liquid vehicle for injection, such as an aqueous vehicle or an oily vehicle, and sterilizing the suspension or solution. An alternative method comprises dispensing a predetermined amount of the compound in each vial, sterilizing the vial and contents, and sealing the vial. For extemporaneous dissolution or blending, a powdery or lyophilized active compound may be accompanied by a spare vial and a vehicle. To isotonize an injection, a nontoxic salt or salt solution can be added. Moreover, stabilizers, preservatives, emulsifiers, and other additives may also be concomitantly used.

Rectal administration can be made by using suppositories which can be manufactured by mixing the compound with a water-soluble or -insoluble low-melting solid base, such as polyethylene glycol, cacao butter, or a higher ester (e.g. myristyl palmitate), or a mixture of them.

As will be described hereinafter, the toxicity of the compound of the present invention is very low.

BEST MODE OF PRACTICING THE INVENTION

The following examples are presented to describe some representative species of the compound of the invention and should by no means be construed as defining the scope of the invention.

The invention will be better understood from the reference examples, working examples, and test examples relevant to the compound of the invention, which are given below.

REFERENCE EXAMPLE 1

Synthesis of (E)-3-(2-phenylethenyl)-2-aminopyridine

In 35 ml of tetrahydrofuran (THF) was dissolved 1.28 g of 2-aminonicotinaldehyde, followed by addition of 2.50 g of diethyl benzylphosphonate and 2.08 g of potassium hydroxide, and the mixture was refluxed at 80° C. for 4.5 hours. This reaction mixture was filtered to remove insoluble matter and the filtrate was evaporated under reduced pressure. The residue was dissolved in 2N-hydrochloric acid and the solution was washed with ether, made basic bv adding 15% aqueous sodium hydroxide solution, and extracted with dichloromethane. The extract was dried over anhydrous magnesium sulfate and the solvent was evaporated off. The residue was recrystallized from acetonitrile to provide 0.83 g of the title compound as yellow prisms. This product was used as a starting material without further purification.

REFERENCE EXAMPLE 2

Synthesis of 2-[2-(4-pyridyl)ethenyl]aniline
(1) Synthesis of 2-[2-(4-pyridyl)ethenyl]-1-nitrobenzene In 120 ml of benzene was suspended 12.00 g of 2-nitrobenzyltriphenylphosphonium bromide and, under argon gas, 20 ml of 1.6M n-butyllithium/n-hexane was added dropwise under ice-cooling with care exercised so that the internal temperature would not rise beyond 20° C. The mixture was then stirred at room temperature for 2 hours, after which 3.05 g of isonicotinaldehyde was added dropwise under ice-cooling and the mixture was stirred at room temperature for another 4 hours. This reaction mixture was poured upon ice-water and extracted with ether. This extract was evaporated under reduced pressure to remove the solvent and the residue was diluted with chloroform and extracted with 2N-hydrochloric acid. The aqueous layer was made basic by adding 30% aqueous sodium hydroxide solution and extracted with chloroform. The chloroform extract was dried over anhydrous magnesium sulfate and the solvent was evaporated off. The residue was purified by silica gel column chromatography (chloroform alone) to provide 2.53 g of the title compound as tan-colored oil. This product was subjected to the next reaction without further purification.

(2) Synthesis of 2-[2-(4-pyridyl)ethenyl]aniline

In a mixture of concentrated hydrochloric acid (14 ml) and ethanol (14 ml) was dissolved 2.87 g of 2-[2-(4-pyridyl)ethenyl]-1-nitrobenzene. To this solution was added a solution of stannous chloride dihydrate (8.59 g) in ethanol (25 ml) gradually dropwise under ice-cooling and the mixture was stirred at room temperature for 5 hours. After the solvent was evaporated off under reduced pressure, the residue was made basic with 30% aqueous sodium hydroxide solution and extracted with chloroform. The extract was dehydrated over anhydrous magnesium sulfate and the solvent was evaporated off to provide 2.2 g of the title compound as yellow solid. This product was used as a starting material without purification.

The following compounds were produced by the same procedure as Reference Example 2.

2-[2-(3-Pyridyl)ethenyl]aniline
2-[2-(2-Pyridyl)ethenyl]aniline
2-[2-(2-Methylpyridin-4-yl)ethenyl]aniline
2-[2-Methyl-2-(4-pyridyl)ethenyl]aniline

REFERENCE EXAMPLE 3

Synthesis of (E)-2-[2-(4-pyridyl)ethenyl]aniline

To 15.1 g of 2-nitrobenzaldehyde was added 9.3 g of 4-picoline followed by addition of 5 ml of acetic anhydride and the mixture was refluxed for 12 hours. This reaction mixture was poured in ice-water, made basic with 2N—NaOH, and extracted with chloroform. The extract was dehydrated over anhydrous magnesium sulfate and the solvent was evaporated off to provide 22.40 g of (E)-2-[2-(4-pyridyl)ethenyl]-1-nitrobenzene. This product was treated as in Reference Example 2 (2) to provide the title compound.

EXAMPLE 1

(E)-2-[[(p-Methoxyphenyl)sulfonyl]amino]-3-(2-phenyl-ethenyl)pyridine

In 10 ml of pyridine was dissolved 0.8 g of the (E)-3-(2-phenylethenyl)-2-aminopyridine obtained in Reference Example 1. To this solution was added 0.92 g of p-methoxyphenylsulfonyl chloride gradually under ice-cooling and the mixture was stirred at room temperature overnight. After completion of the reaction, the solvent was evaporated off and the resulting residue was purified by silica gel column chromatography (eluent: CHCl$_3$/MeOH= 9/1). The crystal crop thus obtained was recrystallized from ethanol to provide 0.77 g of the desired compound (yellow plates). m.p. 152–155° C. Elemental analysis for C$_{20}$H$_{19}$N$_2$O$_3$S Calcd. (%): C, 65.55; H, 4.95; N, 7.64
Found (%): C, 65.40; H, 4.95; N, 7.52

EXAMPLE 2

3-[2-[2-[[(p-Methoxyphenyl)sulfonyl]amino]phenyl]ethenyl]pyridine

Using 2.24 g of 2-[2-(3-pyridyl)ethenyl]aniline prepared as Reference Example 2, the reaction and after-treatment procedure of Example 1 was otherwise carried out to give crystals from E- and Z-fractions. These crystal crops were respectively recrystallized from ethanol to provide 1.51 g of the Z-isomer (white plates) and 0.98 g of the E-isomer (yellow prisms) of the title compound.

Z-isomer
m.p. 131–132° C.
Elemental analysis for C$_{20}$H$_{18}$N$_2$O$_3$S
  Calcd. (%): C, 65.55; H, 4.95; N, 7.64
  Found (%): C, 65.52; H, 5.21; N, 7.64
E-isomer
m.p. 153–154° C.
Elemental analysis for C$_{20}$H$_{18}$N$_2$O$_3$S
  Calcd. (%): C, 65.55; H, 4.95; N, 7.64
  Found (%): C, 65.35; H, 5.17; N, 7.59

EXAMPLE 3A (E)-4-[2-[2-[[(p-Methoxyphenyl)sulfonyl]amino]phenyl]ethenyl]pyridine Using 4.93 g of 2-[2-(4-pyridyl)ethenyl]aniline and 5.70 g of p-methoxybenzenesulfonyl chloride, the reaction and after-treatment procedure of Example 1 was otherwise carried out to give a crystal crop. This crystal crop was recrystallized from ethanol to provide 1.94 g of the title compound (light yellowish white prisms). m.p. 207–209° C.
Elemental analysis for C$_{20}$H$_{18}$N$_2$O$_3$S
  Calcd. (%): C, 65.55; H, 4.95; N, 7.64
  Found (%): C, 65.61; H, 5.06; N, 7.64

EXAMPLE 3B (E)-4-[2-[2-[[(p-Methoxyphenyl)sulfonyl]amino]phenyl]ethenyl]pyridine Hydrochloride One (1.00) compound obtained in Example 3A was dissolved in 100 ml of methanol followed by addition of hydrogen chloride gas-saturated ethereal solution of 5 times as much by volume under ice-cooling. The solvent was then evaporated off to provide 1.07 g of the title compound as yellow powders. m.p. 258–261° C. (decomp.)
Elemental analysis for C$_{20}$H$_{18}$N$_2$O$_3$S.HCl
  Calcd. (%): C, 59.62; H, 4.75; N, 6.95
  Found (%): C, 59.36; H, 4.81; N, 6.90

The following compounds were synthesized in the same manner as Example 1.

EXAMPLE 4

(E)-2-[2-[2-[[(p-Methoxyphenyl)sulfonyl]amino]phenyl]ethenyl]pyridine

Light yellowish white prisms (ethanol), m.p. 137–142° C.
Elemental analysis for C$_{20}$H$_{18}$N$_2$O$_3$S
  Calcd. (%): C, 65.55; H, 4.95; N, 7.64
  Found (%): C, 65.54; H, 5.13; N, 7.60

EXAMPLE 5

(E)-4-[2-[2-[[(p-Methylphenyl)sulfonyl]amino]phenyl]ethenyl]pyridine

Yellowish white needles, m.p. 244–246° C.
Elemental analysis for C$_{20}$H$_{18}$N$_2$O$_2$S
  Calcd. (%): C, 68.55; H, 5.18; N, 7.99
  Found (%): C, 68.41; H, 5.32; N, 7.96

EXAMPLE 6

(E)-4-[2-[2-[[[p-(2-Fluoroethoxy)phenyl]sulfonyl]amino]phenyl]ethenyl]pyridine

Colorless needles, m.p. 174–176° C.
Elemental analysis for C$_{21}$H$_{19}$FN$_2$O$_3$S Calcd. (%): C, 63.30; H, 4.81; N, 7.03
Found (%): C, 63.40; H, 4.86; N, 7.07

EXAMPLE 7

(E)-4-[2-[2-[[(p-Ethoxyphenyl)sulfonyl]amino]
phenyl]ethenyl]pyridine
Light yellow prisms, m.p. 201–203° C.
Elemental analysis for $C_{21}H_{20}N_2O_3S$
  Calcd. (%): C, 66.30; H, 5.30; N, 7.36
  Found (%): C, 66.18; H, 5.18; N, 7.39

EXAMPLE 8

(E)-4-[2-[2-[[(p-Hydroxyphenyl)sulfonyl]amino]
phenyl]ethenyl]pyridine

In DMF was dissolved 2.00 g of the (E)-4-[2-[2-[[(p-methoxyphenyl)sulfonyl]amino]phenyl]ethenyl]pyridine obtained in Example 3, followed by addition of 1.91 g of sodium methanethiolate, and the mixture was stirred at 100° C. overnight and then after-treated. The resulting crystals were recrystallized from methanol to provide 0.19 g of the title compound (white powders).
m.p. 293–296° C. (decomp.)
Elemental analysis for $C_{19}H_{16}N_2O_3S$
  Calcd. (%): C, 64.76; H, 4.58; N, 7.95
  Found (%): C, 64.60; H, 4.41; N, 7.90

EXAMPLE 9

(E)-4-[2-[2-[[N-(2-Fluoroethyl)-N-[(p-methoxyphenyl)sulfonyl]amino]phenyl]ethenyl]
pyridine hydrochloride In 100 ml of acetone was dissolved 0.80 g of the (E)-4-[2-[2-[[(p-methoxyphenyl)sulfonyl]amino]phenyl]ethenyl] pyridine as much as possible. Then, 1.19 g of 1-bromo-2-fluoroethane and 0.60 g of potassium carbonate were added and the mixture was reacted in a sealed reaction tube at 80° C. overnight. After cooling, the solvent was evaporated off under reduced pressure and the residue was diluted with water and extracted with chloroform. The extract was dehydrated over anhydrous magnesium sulfate and the solvent was evaporated off. The residue was purified by silica gel column chromatography (chloroform-methanol=99:1) to provide 0.86 g of light yellow oil. After this oil was dissolved in ether, hydrogen chloride-saturated ether was added under ice-cooling and the resulting yellow powders were recovered by filtration to provide the title compound.
m.p. 218–220° C. (decomp.)
Elemental analysis for $C_{22}H_{21}FN_2O_3S \cdot HCl$
  Calcd. (%): C, 58.86; H, 4.94; N, 6.24
  Found (%): C, 58.74; H, 5.15; N, 6.14

EXAMPLE 10

(E)-2-Methyl-4-[2-[2-[[(p-methoxyphenyl)sulfonyl]
amino]phenyl]ethenyl]pyridine hydrochloride The procedures of Example 1 and Example 3B were essentially carried out to provide the title compound as yellow powders. m.p. 249–252° C. (decomp.)
Elemental analysis for $C_{21}H_{20}N_2O_3S \cdot HCl$
  Calcd. (%): C, 60.50; H, 5.08; N, 6.72
  Found (%): C, 60.36; H, 4.83; N, 6.75

The following compounds were produced by the same procedure as described in Example 1.

EXAMPLE 11

4-[1-Methyl-2-[2-[[(p-methoxyphenyl)sulfonyl]
amino]phenyl]ethenyl]pyridine
Colorless needles, m.p. 174–176° C.
Elemental analysis for $C_{21}H_{20}N_2O_3S \cdot HCl$ Calcd. (%): C, 65.55; H, 4.95; N, 7.64
Found (%): C, 65.69; H, 4.95; N, 7.69

EXAMPLE 12

(E)-4-[2-[2-[[(p-Nitrophenyl)sulfonyl]amino]phenyl]
ethenyl]pyridine
Yellowish white powders (ethanol), m.p. 281–284° C. (decomp.)
Elemental analysis for $C_{19}H_{15}N_3O_4S$
  Calcd. (%): C, 59.83; H, 3.96; N, 11.02
  Found (%): C, 59.72; H, 3.86; N, 10.75

EXAMPLE 13

(E)-4-[2-[2-[[(p-Fluorophenyl)sulfonyl]amino]
phenyl]ethenyl]pyridine
Yellow needles (ethanol), m.p. 272–276° C. (decomp.)
Elemental analysis for $C_{19}H_{15}N_2O_2FS$
  Calcd. (%): C, 64.39; H, 4.27; N, 7.90
  Found (%): C, 64.43; H, 4.18; N, 7.65

The following compounds were obtained in the same manner as Example 10.

EXAMPLE 14

(E)-3-Chloro-4-[2-[2-[[(p-methoxyphenyl)sulfonyl]
amino]phenyl]ethenyl]pyridine Hydrochloride
Light yellow prisms (ethanol), m.p. 208–211° C.
Elemental analysis for $C_{20}H_{17}ClN_2O_3S \cdot HCl$
  Calcd. (%): C, 54.93; H, 4.15; N, 6.41
  Found (%): C, 54.78; H, 4.28; N, 6.54

EXAMPLE 15

(E)-4-[2-[2-[[(p-Methoxyphenyl)sulfonyl]amino]
phenyl]ethenyl]pyrimidine hydrochloride
Yellow prisms (methanol), m.p. 213–215° C. (decomp.)
Elemental analysis for $C_{19}H_{17}N_3O_3S \cdot HCl$
  Calcd. (%): C, 56.50; H, 4.49; N, 10.40
  Found (%): C, 56.64; H, 4.49; N, 10.37

EXAMPLE 16

(E)-2-[2-[2-[[(p-Methoxyphenyl)sulfonyl]amino]
phenyl]ethenyl]pyrazine hydrochloride
Orange-colored prisms (ethanol), m.p. 216–218° C. (decomp.)
Elemental analysis for $C_{19}H_{17}N_3O_3S \cdot HCl$
  Calcd. (%): C, 56.50; H, 4.49; N, 10.40
  Found (%): C, 56.31; H, 4.55; N, 10.29

EXAMPLE 17

(E)-2,6-Dimethyl-4-[2-[2-[[(p-methoxyphenyl)
sulfonyl]amino]phenyl]ethenyl]pyridine
hydrochloride
Yellow powders, m.p. 227–230° C. (decomp.)
Elemental analysis for $C_{22}H_{22}N_2O_3S \cdot HCl$
  Calcd. (%): C, 61.32; H, 5.38; N, 6.50
  Found (%): C, 60.79; H, 5.39; N, 6.50

The following compounds were synthesized by the same procedure as Example 1.

EXAMPLE 18

(E)-2-Methyl-4-[2-[2-[(p-methoxybenzoyl)amino]
phenyl]ethenyl]pyridine
Colorless needles (ethanol), m.p. 183–184° C.
Elemental analysis for $C_{22}H_{20}N_2O_2$ Calcd. (%): C, 76.72; H, 5.85; N, 8.14
Found (%): C, 76.65; H, 5.97; N, 8.12

EXAMPLE 19

(E)-2-Methyl-4-[2-[4-chloro-2-[[(p-methoxyphenyl)
sulfonyl]amino]phenyl]ethenyl]pyridine
Colorless needles, m.p. 174–175° C.
Elemental analysis for $C_{21}H_{19}ClN_2O_3S$
Calcd. (%): C, 60.79; H, 4.62; N, 6.75
Found (%): C, 60.80; H, 4.68; N, 6.71

EXAMPLE 20

(E)-4-[2-[2-[[(p-Methoxyphenyl)sulfonyl]amino]
phenyl]ethenyl]pyridine 1-oxide

In 10 ml of acetic acid was dissolved 1.83 g of the compound obtained in Example 3. Then, 2.80 g of 30% aqueous hydrogen peroxide solution was added and the mixture was stirred at $_{70}$° C. overnight. Saturated aqueous sodium hydrogen carbonate solution was added to the reaction mixture, followed by extraction with chloroform. The chloroform layer was dehydrated over anhydrous magnesium sulfate and the solvent was evaporated off. The residue was purified by silica gel column chromatography (chloroform-methanol=9:1). The crystal crop was recrystallized from ethanol to provide 0.48 g of the title compound (white needles). m.p. 224–226° C. (decomp.)
Elemental analysis for $C_{20}H_{18}N_2O_4S$
Calcd. (%): C, 62.81; H, 4.74; N, 7.32
Found (%): C, 62.71; H, 4.72; N, 7.32
The following compounds were obtained by the same Drocedure as Example 1.

EXAMPLE 21

(E)-3-Methyl-4-[2-[2-[[(p-methoxyphenyl)sulfonyl]
amino]phenyl]ethenyl]pyridine
Yellow-brown prisms (ethanol), m.p. 183–185° C.
Elemental analysis for $C_{21}H_{20}N_2O_3S$
Calcd. (%): C, 66.30; H, 5.30; N, 7.36
Found (%): C, 66.21; H, 5.37; N, 7.38

EXAMPLE 22

(E)-4-[2-[2-[[(p-Methoxyphenyl)sulfonyl]amino]-3-
methoxyphenyl]ethenyl]pyridine
Colorless needles (methanol), m.p. 205–206° C.
Elemental analysis for $C_{21}H_{20}N_2O_4S$
Calcd. (%): C, 63.62; H, 5.08; N, 7.07
Found (%): C, 63.67; H, 5.14; N, 7.07

EXAMPLE 23

(E)-4-[2-[2-[[(p-Chlorophenyl)sulfonyl]amino]
phenyl]ethenyl]pyridine
Light yellow needles (ethanol), m.p. 218–220° C.
Elemental analysis for $C_{19}H_{15}ClN_2O_2S$
Calcd. (%): C, 61.54; H, 4.08; N, 7.55
Found (%): C, 61.74; H., 4.02; N, 7.55

EXAMPLE 24

(E)-4-[2-[2-[[(2,5-Dimethoxyphenyl)sulfonyl]
amino]phenyl]ethenyl]pyridine
Light yellow plates (ethanol), m.p. 193–195° C.
Elemental analysis for $C_{21}H_{20}N_2O_4S$
Calcd. (%): C, 63.62; H, 5.08; N, 7.07
Found (%): C, 63.38; H, 5.07; N, 7.04

EXAMPLE 25

(E)-4-[2-[2-[[(3,4-Dimethoxyphenyl)sulfonyl]
amino]phenyl]ethenyl]pyridine
Light yellow needles (ethanol), m.p. 181–183° C.
Elemental analysis for $C_{21}H_{20}N_2O_4S$
Calcd. (%): C, 63.62; H, 5.08; N, 7.07
Found (%): C, 63.56; H, 5.08; N, 7.07

EXAMPLE 26

(E)-4-[2-[2-[[(p-Hydroxyphenyl)sulfonyl]amino]
phenyl]ethenyl]pyridine 1-oxide

Using 1.50 g of the compound obtained in Example 8, the reaction and after-treatment procedure of Example 20 was otherwise carried out and the resulting crystal crop was recrystallized from methanol to provide 0.23 g of the title compound (white fine needles). m.p. 276–278° C. (decomp.)
Elemental analysis for $C_{19}H_{16}N_2O_4S$
Calcd. (%): C, 61.94; H, 4.38; N, 7.60
Found (%): C, 61.96; H, 4.36; N, 7.58
The following compounds were obtained by the same procedure as Example 1.

EXAMPLE 27

(E)-4-[2-[4-Chloro-2-[[(p-methoxyphenyl)sulfonyl]
amino]phenyl]ethenyl]pyridine
Colorless needles (methanol), m.p. 190–193° C.
Elemental analysis for $C_{20}H_{17}ClN_2O_3S$
Calcd. (%): C, 59.92; H, 4.27; N, 6.99
Found (%): C, 59.82; H, 4.26; N, 7.01

EXAMPLE 28

(E)-4-[2-[5-Chloro-2-[[(p-methoxyphenyl)sulfonyl]
amino]phenyl]ethenyl]pyridine
Colorless prisms (ethanol), m.p. 175–176° C.
Elemental analysis for $C_{20}H_{17}ClN_2O_3S$
Calcd. (%): C, 59.92; H, 4.27; N, 6.99
Found (%): C, 59.87; H, 4.29; N, 6.97

EXAMPLE 29

(E)-4-[2-[2-[N-(3,4,4-Trifluoro-3-butenyl)-N-[(p-
methoxyphenyl)sulfonyl]amino]phenyl]ethenyl]
pyridine In tetrahydrofuran was dissolved 1.83 g of the compound obtained in Example 3. To this solution were added 1.89 g of 3,4,4-trifluoro-3-butenyl bromide and 1.38 g of potassium carbonate and the mixture was reacted in a sealed reaction tube at 80° C. overnight and, then, after-treated. The crystal crod was recrystallized from ethanol to provide 1.07 g of the title compound (light red prisms). m.p. 148–149° C.
Elemental analysis for $C_{24}H_{21}F_3N_2O_3S$
Calcd. (%): C, 60.75; H, 4.46; N, 5.90
Found (%): C, 60.82; H, 4.43; N, 5.97

EXAMPLE 30

(E)-4-[2-[2-[N-(3,3,4,4-Tetrafluorobutyl)-N-[(p-
methoxyphenyl)sulfonyl]amino]phenyl]ethenyl]
pyridine Using 1.00 g of the compound obtained in Example 3, the reaction and after-treatment procedure of Example 9 was otherwise carried out to provide a crystal crop. This crystal crop was recrystallized from ethanol-ether to provide 0.61 g of the title compound (light yellow prisms). m.p. 124–126° C. Elemental analysis for $C_{24}H_{22}F_4N_2O_3S$ Calcd. (%): C, 58.29; H, 4.48; N, 5.66
Found (%): C, 58.29; H, 4.41; N, 5.55

EXAMPLE 31

(E)-4-[2-[2-[N-(3,3,3-Trifluoropropyl)-N-[(p-methoxyphenyl)sulfonyl]amino]phenyl]ethenyl]pyridine Using 1.00 g of the compound obtained in Example 3, the reaction and after-treatment procedure of Example 9 was otherwise carried out to provide a crystal crop. This crystal crop was recrystallized from ethanol to provide 0.39 g of the title compound (white needles). m.p. 124–126° C.
Elemental analysis for $C_{23}H_{21}F_3N_2O_3S$ Calcd. (%): C, 59.73; H, 4.58; N, 6.06
Found (%): C, 59.35; H, 4.75; N, 5.93

The following compounds were obtained by the same procedure as Example 1.

EXAMPLE 32

(E)-4-[2-[2-[[(p-Methoxyphenyl)sulfonyl]amino]-4,5-methylenedioxyphenyl]ethenyl]pyridine
Yellow prisms (ethanol), m.p. 163–165° C.
Elemental analysis for $C_{21}H_{18}N_2O_5S.¼ H_2O$ Calcd. (%): C, 60.79; H, 4.49; N, 6.75
Found (%): C, 60.87; H, 4.95; N, 6.44

EXAMPLE 33

(E)-4-[2-[2-[[(p-Methoxyphenyl)sulfonyl]amino]-4,5-dimethoxyphenyl]ethenyl]pyridine
Light yellow needles (ethanol), m.p. 209–211° C. (decomp.)
Elemental analysis for $C_{22}H_{22}N_2O_5S$ Calcd. (%): C, 61.96; H, 5.20; N, 6.57
Found (%): C, 61.78; H, 5.36; N, 6.58

EXAMPLE 34

(E)-4-[2-[2-[N-(2-Hydroxyethyl)-N-[(p-methoxyphenyl)sulfonyl]amino]phenyl]ethenyl]pyridine Using 1.00 g of the compound obtained in Example 3, the reaction and after-treatment procedure of Example 9 was otherwise carried out to provide a crystal crop. This crystal crop was recrystallized from ethanol to provide 0.57 g of the title compound (white needles). m.p. 198–200° C.
Elemental analysis for $C_{22}H_{22}N_2O_4S$ Calcd. (%): C, 64.37; H, 5.40; N, 6.82
Found (%): C, 64.14; H, 5.48; N, 6.76

EXAMPLE 35

(E)-4-[2-[2-[N-(2-Dimethylaminoethyl)-N-[(p-methoxyphenyl)sulfonyl]amino]phenyl]ethenyl]pyridine]hydrochloride To 1.00 g of the compound obtained in Example 3 was added 1.07 g of triphenylphosphine as well as tetrahydrofuran. Then, 0.30 g of dimethylaminoethanol and 0.72 g of diethyl azodicarboxylate were added in the order mentioned. The reaction was conducted at room temperature overnight and the reaction mixture was after-treated and converted to the hydrochloride. By this procedure, 0.23 g of the title compound (white powders) was obtained. m.p. 259–261° C. (decomp.)
Elemental analysis for $C_{24}H_{27}N_3O_3S.2HCl.H_2O$ Calcd. (%): C, 54.54; H, 5.53; N, 7.95
Found (%): C, 54.54; H, 5.85; N, 7.94

EXAMPLE 36

(E)-4-[2-[2-[N-(2-Aminoethyl)-N-[(p-methoxyphenyl)sulfonyl]amino]phenyl]ethenyl]pyridine Hydrochloride Using 1.00 g of the compound obtained in Example 3, the reaction and after-treatment procedure of ExamDle 35 was otherwise carried out. Thereafter, the amino-protecting group was eliminated by acid treatment. The deprotected compound was then converted to the hydrochloride to provide 0.21 g of the title compound (light yellow powder). m.p. 233–235° C. (decomp.)
Elemental analysis for $C_{22}H_{23}N_3O_3S.2HCl.3/2H_2O$ Calcd. (%): C, 51.86; H, 5.53; N, 8.25
Found (%): C, 51.68; H, 5.65; N, 8.51

The following compounds were obtained by the same procedure as Example 1.

Example 37

(E)-4-[2-[2-[[(p-Trifluoromethoxyphenyl)sulfonyl]amino]phenyl]ethenyl]pyridine
Light yellowish white needles (2-propanol), m.p. 151–153° C.
Elemental analysis for $C_{20}H_{15}F_3N_2O_3S$ Calcd. (%): C, 57.14; H, 3.60; N, 6.66
Found (%): C, 57.17; H, 3.74; N, 6.72

EXAMPLE 38

(E)-4-[2-[2-[[(p-Ethylphenyl)sulfonyl]amino]phenyl]ethenyl]pyridine
Yellow prisms (ethanol), m.p. 232–234° C.
Elemental analysis for $C_{21}H_{20}N_2O_2S$ Calcd. (%): C, 69.21; H, 5.53; N, 7.69
Found (%): C, 69.08; H, 5.63; N, 7.68

EXAMPLE 39

(E)-4-[2-[3-[[(p-Methoxyphenyl)sulfonyl]amino]-2-pyridyl]ethenyl]phenol

Using 0.90 g of 3-amino-2-[2-(4-hydroxyphenyl)ethenyl]pyridine, the reaction and after-treatment procedure of Example 1 was otherwise carried out, and the crystal crop was recrystallized from ethanol to provide 0.16 g of the title compound (yellow flocs). m.p. 217–219° C.
Elemental analysis for $C_{20}H_{18}N_2O_4S$ Calcd. (%): C, 62.81; H, 4.74; N, 7.32
Found (%): C, 62.62; H, 4.79; N, 7.42

EXAMPLE 40

(E)-4-[2-[3-[[(p-Methoxyphenyl)sulfonyl]amino]-2-pyridyl]ethenyl]phenol hydrochloride A 0.74 g portion of the compound obtained in Example 39 was converted to the hydrochloride to provide 0.37 g of the title compound (yellow fine needles). m.p. 222–224° C. (decomp.)
Elemental analysis for $C_{20}H_{18}N_2O_4S.HCl$ Calcd. (%): C, 57.35; H, 4.57; N, 6.69

Found (%): C, 56.93; H, 4.66; N, 6.68

The following compounds were obtained by the same procedure as Example 1.

EXAMPLE 41

(E)-4-[2-[6-Chloro-2-[[(p-methoxyphenyl)sulfonyl]amino]phenyl]ethenyl]pyridine

Light yellow plates (ethanol), m.p. 188–190° C.
Elemental analysis for $C_{20}H_{17}ClN_2O_3S$
  Calcd. (%): C, 59.92; H, 4.27; N, 6.99
  Found (%): C, 59.82; H, 4.26; N, 6.95

EXAMPLE 42

(E)-4-[2-[[2-[(p-Methoxyphenyl)sulfonyl]amino]-3,4-methylenedioxyphenyl]ethenyl]pyridine Orange-colored needles (ethanol), m.p. 279–281° C. (decomp.)
Elemental analysis for $C_{21}H_{18}N_2O_5S \cdot 2H_2O$
  Calcd. (%): C, 56.49; H, 4.97; N, 6.27
  Found (%): C, 56.21; H, 4.63; N, 6.36

EXAMPLE 43

(E)-4-[2-[6-Fluoro-2-[[(p-methoxyphenyl)sulfonyl]amino]phenyl]ethenyl]pyridine

Colorless prisms (ethanol), m.p. 177–178° C.
Elemental analysis for $C_{20}H_{17}FN_2O_3S$
  Calcd. (%): C, 62.47; H, 4.46; N, 7.29
  Found (%): C, 62.48; H, 4.49; N, 7.31

EXAMPLE 44

(E)-4-[2-[3-Methyl-2-[[(p-methoxyphenyl)sulfonyl]amino]phenyl]ethenyl]pyridine hydrochloride By the same procedures as Example 1 and Example 3B, orange-colored needles were obtained. m.p. ≧250° C.
IR (KBr) $cm^{-1}$: 1622, 1593, 1499, 1323, 1262, 1148, 1094, 941, 814, 669, 583, 550
Elemental analysis for $C_{21}H_{20}N_2O_3S \cdot HCl$
  Calcd. (%): C, 60.50; H, 5.08; N, 6.72
  Found (%): C, 60.44; H, 5.10; N, 6.68

EXAMPLE 45

(E)-4-[2-[2-[[[4-(2-Fluoroethoxy)phenyl]sulfonyl]amino]phenyl]ethenyl]pyridine 1-oxide Using 3.18 g of the compound obtained in Example 6, the reaction and after-treatment procedure of Example 20 was otherwise carried out to provide a crystal crop. This crystal crop was recrystallized from methanol to provide 1.21 g of the title compound (colorless prisms). m.p. 214–215° C.
Elemental analysis for $C_{21}H_{19}FN_2O_4S$
  Calcd. (%): C, 60.86; H, 4.62; N, 6.76
  Found (%): C, 60.84; H, 4.55; N, 6.86

EXAMPLE 46

(E)-4-[2-[2-[[(p-Ethoxyphenyl)sulfonyl]amino]phenyl]ethenyl]pyridine 1-oxide

Using 3.18 g of the compound obtained in Example 6, the reaction and after-treatment procedure of Example 20 was otherwise carried out to provide a crystal crop. This crystal crop was recrystallized from methanol to provide 1.52 g of the title compound (colorless prisms). m.p. 223–225° C.
Elemental analysis for $C_{21}H_{20}N_2O_4S$
  Calcd. (%): C, 63.62; H, 5.08; N, 7.07
  Found (%): C, 63.58; H, 5.07; N, 7.11

EXAMPLE 47

(E)-4-[2-[2-[[(p-Methoxyphenyl)sulfonyl]amino]-3-methoxyphenyl]ethenyl]pyridine 1-oxide Using 3.17 g of the compound obtained in Example 22, the reaction and after-treatment procedure of Example 20 was otherwise carried out to provide a crystal crop. This crystal crop was recrystallized from ethanol to provide 2.10 g of the title compound (colorless prisms). m.p. 233–234° C. (decomp.)
Elemental analysis for $C_{21}H_{20}N_2O_5S$
  Calcd. (%): C, 61.15; H, 4.89; N, 6.79
  Found (%): C, 61.04; H, 4.85; N, 6.86

EXAMPLE 48

(E)-4-[2-[2-[N-(2-Hydroxyethyl)-N-[(p-ethoxyphenyl)sulfonyl]amino]phenyl]ethenyl]pyridine Using 1.00 g of the compound obtained in Example 7, the reaction and after-treatment procedure of Example 9 was otherwise carried out to provide a crystal crop. This crystal crop was recrystallized from ethanol to provide 0.56 g of the title compound (light yellow prisms). m.p. 167–169° C.
Elemental analysis for $C_{23}H_{24}N_2O_4S$
  Calcd. (%): C, 65.07; H, 5.70; N, 6.60
  Found (%): C, 64.93; H, 5.80; N, 6.60

EXAMPLE 49

(E)-4-[2-[2-[N-(2-Hydroxyethyl)-N-[(p-methoxyphenyl)sulfonyl]amino]phenyl]ethenyl]pyridine 1-oxide Using 1.00 g of the compound obtained in Example 20, the reaction and after-treatment Drocedure of Example 9 was otherwise carried out to provide a crystal crop. This crystal crop was recrystallized from ethanol to provide 0.17 g of the title compound (yellow plates). m.p. 219–221° C.
Elemental analysis for $C_{22}H_{22}N_2O_5S$
  Calcd. (%): C, 61.96; H, 5.20; N, 6.57
  Found (%): C, 61.77; H, 5.32; N, 6.57

EXAMPLE 50

(E)-4-[2-[2-[N-(2-Hydroxyethyl)-N-[p-[(2-fluoroethoxy)phenyl]sulfonyl]amino]phenyl]ethenyl]pyridine Using 1.00 g of the compound obtained in Example 6, the reaction and after-treatment procedure of Example 9 was otherwise carried out to provide a crystal crop. This crystal crop was recrystallized from ethanol to provide 0.59 g of the title compound (light yellow fine needles). m.p. 180–182° C.
Elemental analysis for $C_{23}H_{23}FN_2O_4S$
  Calcd. (%): C, 62.43; H, 5.24; N, 6.33
  Found (%): C, 62.36; H, 5.27; N, 6.29

EXAMPLE 51

(E)-4-[2-[2-[N-[2-(4-Morpholino)ethyl]-N-[(p-methoxyphenyl)sulfonyl]amino]phenyl]ethenyl]pyridine Using 1.00 g of the compound obtained in Example 3, the reaction and after-treatment procedure of Example 35 was otherwise carried out to provide a crystal crop. This crystal crop was recrystallized from ethanol to provide 0.75 g of the title compound (white prisms). m.p. 142–144° C.
Elemental analysis for $C_{26}H_{29}N_3O_4S$
  Calcd. (%): C, 65.11; H, 6.09; N, 8.76
  Found (%): C, 64.93; H, 6.06; N, 8.71

EXAMPLE 52

(E)-4-[2-[6-Fluoro-2-[N-(2-hydroxyethyl)-N-[(p-methoxyphenyl)sulfonyl]amino]phenyl]ethenyl] pyridine In tetrahydrofuran was dissolved 1.92 g of the compound obtained in Example 43, followed by addition of 1.72 g of 2-iodoethanol and 0.69 g of potassium carbonate. The mixture was refluxed overnight and after-treated to give crystals. This crystal crop was recrystallized from ethanol to provide 0.46 g of the title compound,(light yellow needles). m.p. 152–153° C.
Elemental analysis for $C_{22}H_{21}FN_2O_4S$
  Calcd. (%): C, 61.67; H, 4.97; N, 6.54
  Found (%): C, 61.51; H, 4.93; N, 6.62

The following compounds were obtained by the same procedure as Example 1.

EXAMPLE 53

(E)-4-[2-[2-[[(p-Methoxyphenyl)sulfonyl]amino]-3-hydroxyphenyl]ethenyl]pyridine
Yellow needles (methanol), m.p. 204–205° C. (decomp.)
Elemental analysis for $C_{22}H_{21}FN_2O_4S$
  Calcd. (%): C, 62.81; H, 4.74; N, 7.32
  Found (%): C, 62.65; H, 4.81; N, 7.22

EXAMPLE 54

(E)-4-[2-[2-[[(p-Methoxyphenyl)sulfonyl]amino]-5-hydroxyphenyl]ethenyl]pyridine
Yellow fine needles (ethanol), m.p. 244–246° C. (decomp.)
Elemental analysis for $C_{20}H_{18}N_2O_4S$
  Calcd. (%): C, 62,81; H, 4.74; N, 7.32
  Found (%): C, 62.62; H, 4.58; N, 7.38

EXAMPLE 55

(E)-4-[2-[2-[N-(2-Methoxyethyl)-N-[(p-methoxyphenyl)sulfonyl]amino]phenyl]ethenyl] pyridine hydrochloride Using 1.00 g of the compound obtained in Example 3A and 1-bromo-2-methoxyethane, the reaction and after-treatment procedure of Example 9 was otherwise carried out and the product was converted to the hydrochloride. By this procedure, 0.45 g of the title compound (amorphous) was obtained.
IR (KBr) cm$^{-1}$: 1662, 1595, 1499, 1343, 1262, 1157, 1020, 806, 722, 586, 552
Elemental analysis for $C_{23}H_{24}N_2O_4S\cdot HCl\cdot\frac{1}{2}H_2O$
  Calcd. (%): C, 58.77; H, 5.58; N, 5.96
  Found (%): C, 58.55; H, 5.62; N, 6.22

EXAMPLE 56

(E)-4-[2-[2-[[N-(2-Hydroxyethyl)-N-[(p-methoxyphenyl)sulfonyl]amino]-3-methoxy]phenyl] ethenyl]pyridine Using 1.00 g of the comDound obtained in Example 22, the reaction and after-treatment procedure of Example 9 was otherwise carried out to provide a crystal crop. This crystal crop was recrystallized from ethanol to provide 0.50 g of the title compound (Light yellow needles). m.p. 170–172° C.
Elemental analysis for $C_{23}H_{24}N_2O_5S$
  Calcd. (%): C, 62.71; H, 5.49; N, 6.36
  Found (%): C, 62.64; H, 5.41; N, 6.60

EXAMPLE 57

(E)-4-[2-[2-[N-Acetyl-N-[(p-methoxyphenyl) sulfonyl]amino]phenyl]ethenyl]pyridine 1-oxide Using 1.54 g of the compound obtained in Example 20, the reaction was conducted in the presence of acetic anhydride at 140° C. for 10 minutes and, then, after-treated. The crystal crop was recrystallized from ethanol to provide 0.62 g of the title compound (white granules). m.p. 235–237° C. (decomp.)
Elemental analysis for $C_{22}H_{20}N_2O_5S$
  Calcd. (%): C, 64.37; H, 5.40; N, 6.82
  Found (%): C, 64.11; H, 5.12; N, 6.85

EXAMPLE 58

(E)-4-[2-[2-[N-(3-Hydroxypropyl)-N-[(p-methoxyphenyl)sulfonyl]amino]phenyl]ethenyl] pyridine Using 1.89 g of the compound obtained in Example 3, the reaction and after-treatment procedure of ExamDle 9 was otherwise carried out to provide 1.89 g of the title compound (white granules). m.p. 164–167° C.
Elemental analysis for $C_{23}H_{24}N_2O_4S$
  Calcd. (%): C, 65.07; H, 5.70; N, 6.60
  Found (%): C, 65.38; H, 5.53; N, 6.80

EXAMPLE 59

(E)-1-Benzyl-4-[2-[2-[[(p-methoxyphenyl)sulfonyl] amino]phenyl]ethenyl]pyridinium Bromide To 1.00 g of the compound obtained in Example 3 was added 25 ml of benzyl bromide and the reaction was carried out at 120° C. overnight. The reaction mixture was after-treated and the crystals were recrystallized from methanol to provide 0.62 g of the title compound (yellow fine needles). m.p. ≧280° C. IR (KBr) cm$^{-1}$: 1620, 1597, 1518, 1327, 1266, 1156, 1092, 598, 571
Elemental analysis for $C_{27}H_{25}BrN_2O_3S$
  Calcd. (%): C, 60.34; H, 4.69; N, 5.21
  Found (%): C, 60.18; H, 4.55; N, 5.39

The anticancer activity of the compound of the present invention could be confirmed by the following tests. The test methods used were those which are being used most broadly in in vitro and in vivo evaluations today. [in vitro method: European Journal of Cancer 1980, 17, 129; in vivo method: Cancer Research 1988, 48, 589–601].

TEST EXAMPLE 1

In Vitro anticancer effects on KB (human nasopharynx carcinoma), Colon 38 (mouse colon cancer), and WiDr (human colorectal cancer) cell lines Each of KB, Colon 38, and WiDr cell lines were respectively cultured using 10% fetal calf serum-supplemented D-MEM medium (Nissui Pharmaceutical). Each monolayer of cells was exfoliated with a 50:50 (v/v) mixture of 0.25% trypsin and 0.02% ethylenediaminetetracetic acid and after inactivation of trypsin, the cells were collected by centrifuging at 800 rpm for 3 minutes and suspended in the same medium as above. Using a hemocytometer, the number of the cells in the suspension were counted. The suspension was diluted with the medium to $5 \times 10^4$ cells/ml and distributed to a 96-well flat-bottomed plate, 100 μl per well.

The test drug was first dissolved in dimethyl sulfoxide at a concentration of 2 mg/ml and diluted with the above medium to 20 μg/ml. Using this solution for the highest concentration, a doubling dilution series was prepared and 100 μl of each dilution was added to the above cell suspension.

The plate was then incubated under 5% $CO_2$-air at 37° C. for 72 hours. Then, a 5 mg/ml solution of MTT [3-(4,5-dimethylthiazol-2-yl)-2,5-diphenyltetrazolium bromide] was added to the plate, 30 μl per well and the reaction was carried out under 5% $CO_2$-air at 37° C. for 4 hours. After the reaction, the solution in each well was aspirated off and 100 μl/well of dimethyl sulfoxide was added. After 5 minutes of shaking, the absorbance at 540 nm was measured with a Multiscan (Titertek) and the 50% cell growth-inhibitory concentration ($IC_{50}$) was calculated. The $IC_{50}$ values thus determined are presented in Table 1.

TABLE 1

| Compound | $IC_{50}$ μg/ml | | |
|---|---|---|---|
| | KB | Colon 38 | WiDr |
| Example 1 | 0.44 | 0.75 | 0.45 |
| Example 2 (cis) | 4.86 | 6.48 | 4.81 |
| Example 2 (trans) | 0.10 | 0.15 | 0.09 |
| Example 3A | 0.0026 | 0.0031 | 0.0025 |
| Example 4 | 0.12 | 0.16 | 0.16 |

TEST EXAMPLE 2
Microtubule polymerization-inhibitory activity Microtubule polymerization-inhibitory activity A microtubule protein (a mixed solution of microtubule protein and microtubule-bound protein) was purified from a crude porcine brain extract according to the method of Williams et al. [Method in Enzymology, 85, 36, 1982] to isolate and the microtubule polymerization inhibitory activity of the compound of the invention was studied. The microtubule protein solution was diluted to 4 mg/ml as purified microtubule protein with GTP (guanosine-5'-triphosphate)-added reaction buffer (pH 6.8) {100 mM MES [2-(N-morpholinoethanesulfonic acid], 0.5 mM $MgCl_2$-1 mM EGTA (ethylene glycol bis(β-aminoethyl ether)-N,N, N',N'-tetracetic acid), 1 mM GTP} under ice-cooling and after degassing in ice, the test drug was added. Using a spectrophotometer maintained at 37° C., the absorbance of the system at 350 nm was measured at 2-minute intervals for 30 minutes to construct a polymerization curve and the concentration corresponding to 50% inhibition of microtubule protein polymerization was calculated. As the test drug, the compound of Example 3A was used.

As assayed by the above procedure, the 50% inhibitory concentration against microtubule protein polymerization of the compound of Example 3A was 11.2 μM.

TEST EXAMPLE 3
Growth inhibitory activity against WiDr tumor cells transplanted in nude mice The tumor subcutaneously subcultured in nude mice (BALB/c nu/nu, male) aged 5–7 weeks were excised. After removal of the skin and connective tissue around the tumor, the tumor mass was split to remove the central necrotic tissue and, then, cut into cubes with a 2 mm side. One cube was loaded into a grafting needle and transplanted subcutaneously in the right thoracic region of the nude mouse. The major and minor diameters of the tumor were measured with calipers and the tumor volume was calculated by means of Equation 1. Starting when the volume had reached about 100 $mm^3$, the mice were divided into 6 individuals per group and the test drug suspended in 0.5% methylcellulose solution was administered orally by gastric gavage once daily.

Volume=½×major diameter×(minor diameter)²     Equation 1

The tumor volume was determined by the above method at predetermined intervals. From the tumor volume thus calculated, the growth rate was calculated by means of Equation 2. Then, using Equation 3, the growth inhibition rate in each drug treatment group relative to the control group was calculated.

Growth rate=tumor volume at day n/tumor volume at initiation of administration     Equation 2

Growth inhibition rate (%)=(1−growth rate in drug treatment group/growth rate in control group)×100     Equation 3

As the the test compound, the compound of Example 3A was used. The results are shown in Table 2.

TABLE 2

| Dosage mg/kg/day | Growth inhibition rate (%) at day 16 after initiation of administration | Survival rate |
|---|---|---|
| 10 | 16.4 | 6/6 |
| 30 | 57.0 | 6/6 |
| 100 | 81.7 | 6/6 |

In this experiment, 100 mg/kg of the compound of Example 3A was administered orally once daily for 14 days but no death occurred by the end of the administration period.

TEST EXAMPLE 4
Anticancer activity against Colon-26 (mouse colon cancer) cells transplanted in mice Using an injection syringe, Colon-26 cells cultured in vitro were transplanted subcutaneously in a dose of $5 \times 10^5$/animal in the right thoracic region of BALB/c mice (5 weeks old, male). As in Test Example 3, the mice were divided into groups of 6 when the tumor volume had reached about 150 $mm^3$. Starting the following day, the test drug suspended in 0.5% methylcellulose solution was administered orally by gastric gavage once daily for 8 days. The tumor volume was measured at a predetermined interval by the same method as in Test Example 3 and the tumor growth inhibition rate in each drug treatment group relative to the control group was calculated. As the test compound, the compound of Example 3A was used. The results are shown in Table 3.

TABLE 3

| Dosage mg/kg/day | Growth inhibition rate (%) at day 13 after initiation of administration | Survival rate |
|---|---|---|
| 25 | 44.8 | 6/6 |
| 50 | 95.3 | 5/6 |

TEST EXAMPLE 5
In vivo anticancer activity against mouse monocytic leukemia P-388 cell line A suspension of tumor cells was transplanted intraperitoneally in CDF$_1$ mice in a dose of $10^6$ cells/animal. On the following day and after 5 days, or twice, the test drug suspended in 0.5% methylcellulose solution was administered orally. The experiment was performed in 8–12 mice for each control group and 6 mice for each drug treatment group.

For evaluation, the median survival time in days was determined for each drug treatment group (T) and control group (C) and T/C (%) was calculated. The results are presented in Table 4.

TABLE 4

| Compound | Dosage (mg/kg) | T/C (%) |
|---|---|---|
| Example 3B | 25 | 116 |
| | 50 | 126 |
| | 100 | 168 |
| | 200 | 221 |
| Example 20 | 25 | 135 |
| | 50 | 115 |
| | 100 | 180 |
| | 200 | 195 |
| Example 34 | 25 | 105 |
| | 50 | 124 |
| | 100 | 167 |
| | 200 | 210 |
| Example 49 | 100 | 185 |
| | 200 | 220 |
| Example 57 | 25 | 115 |
| | 50 | 160 |
| | 100 | 215 |
| | 200 | 250 |

TEST EXAMPLE 6

Acute toxicity

Male 5-week-old CDF$_1$ mice were used. After the compound of Example 3B or 34 was orally administered once, the mortality rate was investigated after 2 weeks and the LD$_{50}$ value was calculated by the probit method. As a result, the LD$_{50}$ value of the compound of Example 3B was found to be 510 mg/kg and that of the compound of Example 34 was found to be 754 mg/kg. The high safety of the compound of the invention is obvious.

The results of the above Test Examples 1 through 6 indicate clearly that the compound of the present invention has remarkably high anticancer efficacy and is only sparingly toxic.

FORMULATION EXAMPLE 1

| Tablets (oral tablets) | In 180 mg per tablet |
|---|---|
| Compound of Example 3 | 10 mg |
| Lactose | 100 mg |
| Corn starch | 55 mg |
| Low-substitution-degree hydroxypropylcellulose | 9 mg |
| Polyvinyl alcohol (partial hydrolysate) | 5 mg |
| Magnesium stearate | 1 mg |
| | 180 mg |

The above components excepting polyvinyl alcohol and magnesium stearate were evenly mixed and using an aqueous solution of polyvinyl alcohol as a binder, granules for tablet-making were prepared by wet granulation. To the resulting granules were added magnesium stearate and the mixture was compressed with a tablet machine to provide oral tablets measuring 8 mm in diameter and each weighing 180 mg.

FORMULATION EXAMPLE 2

| Hard capsules | In 220 mg per capsule |
|---|---|
| Compound of Example 3A | 10 mg |
| Lactose | 187 mg |
| Microcrystalline cellulose | 20 mg |
| Magnesium stearate | 3 mg |
| | 220 mg |

The above components were evenly mixed and using a capsule-filling machine, the mixture was filled in No. 2 capsule shells, 220 mg per capsule, to provide hard capsules.

FORMULATION EXAMPLE 3

| Granules | In 1 g of granules |
|---|---|
| Compound of Example 3A | 10 mg |
| Lactose | 880 mg |
| Low-substitution-degree hydroxypropylcellulose | 70 mg |
| Hydroxypropylcellulose | 40 mg |
| | 1000 mg |

The above components were evenly mixed followed by kneading, and using a granulator, the kneaded mass was granulated to a diameter of 0.7 mm to provide granules.

INDUSTRIAL APPLICABILITY

The compound of the present invention has potent tubulin polymerization inhibitory activity and anticancer activity with a low toxic potential and can be administered orally. Therefore, the compound can be safely used on a long-term basis for the treatment of various malignant tumors such as lung cancer, breast cancer, gastrointestinal cancer, prostate cancer, and blood cancer, among other malignant tumoral diseases.

What is claimed is:

1. A compound of the following general formula [I] or a hydrate thereof, or a pharmaceutically acceptable salt thereof:

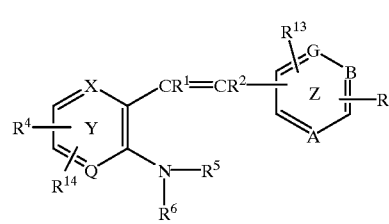

[I]

wherein R$^1$ and R$^2$ may be the same or different and each represents hydrogen, alkyl of 1–6 carbon atoms, acyl of 1–6 carbon atoms, cyano, or —COOR, wherein R represents hydrogen or C$_{1-6}$ alkyl;

wherein R$^3$, R$^4$, R$^{13}$, and R$^{14}$ may be the same or different and each represents hydrogen, alkyl of 1–6 carbon atoms, alkoxy of 1–6 carbon atoms, haloalkoxy of 1–6 carbon atoms, acyl of 1–6 carbon atoms, acyloxy of 1–6 carbon atoms, hydroxy, halogen, nitro, cyano, amino, acylamino of 1–6 carbon atoms, aminoalkyloxy of 1–6 carbon atoms, or morpholinoalkyloxy, the alkyl moiety of which contains 1–6 carbon atoms; and wherein $R^3$ and $R^{13}$ or $R^4$ and $R^{14}$ may jointly represent methylenedioxy;

wherein $R^5$ represents any one of (1) hydrogen, (2) alkyl of 1–6 carbon atoms which is optionally substituted by halogen, amino, monoalkylamino of 1–6 carbon atoms, dialkylamino of 1–6 carbon atoms, morpholino, alkoxy of 1–6 carbon atoms, or hydroxy, (3) alkenyl of 2–6 carbon atoms which is optionally substituted by halogen, (4) alkynyl of 2–6 carbon atoms (5) acyl of 1–6 carbon atoms;

wherein $R^6$ represents any one of (1) aroyl of 7–11 carbon atoms which is optionally substituted by alkyl of 1–6 carbon atoms, alkoxy of 1–6 carbon atoms, or halogen or (2) arylsulfonyl of 6–10 carbon atoms which is optionally substituted by alkyl of 1–6 carbon atoms, alkoxy of 1–6 carbon atoms, haloalkoxy of 1–6 carbon atoms, hydroxy, nitro, or halogen;

wherein A, B, G, Q, and X may be the same or different and each represents any one of N, CH, N→O or $N^+$-$(R^7)E^-$, wherein $R^7$ represents alkyl of 1–6 carbon atoms or arylalkyl of 7–14 carbon atoms and $E^-$ represents an anion; excluded is the case in which A, B, and G concurrently represent N and the case in which A, B, G, Q, and X concurrently represent CH;

and wherein Y and Z independently represent a ring.

2. The compound of claim 1 or a hydrate thereof, or a pharmaceutically acceptable salt thereof, wherein $R^1$ and $R^2$ independently represent hydrogen; wherein $R^3$, $R^4$, $R^{13}$, and $R^{14}$ may be the same or different and each represents hydrogen, acyl of 1–3 carbon atoms, halogen, or hydroxy; wherein $R^5$ represents hydrogen, acyl of 2–4 carbon atoms, hydroxy-substituted alkyl of 1–3 carbon atoms; wherein $R^6$ represents benzenesulfonyl substituted by alkoxy of 1–3 carbon atoms; wherein ring Y represents phenyl; and wherein ring Z represents 4-pyridyl or 1-oxide-4-pyridyl.

3. The compound of claim 1 or a hydrate thereof, or a pharmaceutically acceptable salt thereof, wherein $R^1$ and $R^2$ independently represent hydrogen; wherein $R^3$, $R^4$, $R^{13}$, and $R^{14}$ may be the same or different and each represents hydrogen, acetyl, fluorine or hydroxy; wherein $R^5$ represents hydrogen, acetyl, or ethyl substituted by hydroxy; wherein $R^6$ represents benezenesulfonyl substituted by methoxy; wherein ring Y represents phenyl; and wherein ring Z represents 4-pyridyl or its 1-oxide-4-pyridyl.

4. The compound of claim 1 which is selected from the group consisting of (E)-4-[2-[2-[[(p-methoxyphenyl)sulfonyl]amino]phenyl]ethenyl]pyridine, (E)-4-[2-[2-[[(p-methoxyphenyl)sulfonyl]amino]phenyl]ethenyl]pyridine 1-oxide, (E)-4-[2-[2-[N-(2-hydroxyethyl)-N-[(p-methoxyphenyl)sulfonyl]amino]phenyl]ethenyl]pyridine 1-oxide, (E)-4-[2-[2-[N-(2-hydroxyethyl)-N-[(p-methoxyphenyl)sulfonyl]amino]phenyl]ethenyl]pyridine and (E)-4-[2-[2-[N-acetyl-N-[(p-methoxyphenyl)sulfonyl]amino]phenyl]ethenyl]pyridine 1-oxide, inclusive of their hydrates and their salts.

5. The compound of claim 1 which is selected from the group consisting of (E)-4-[2-[2-[[(p-methoxyphenyl)sulfonyl]amino]phenyl]ethenyl]pyridine, (E)-4-[2-[2-[N-(2-hydroxyethyl)-N-[(p-methoxyphenyl)sulfonyl]amino]phenyl]ethenyl]pyridine 1-oxide, (E)-4-[2-[2-[N-(2-hydroxyethyl)-N-[(p-methoxyphenyl)sulfonyl]amino]phenyl]ethenyl]pyridine, and (E)-4-[2-[2-[N-acetyl-N-[(p-methoxyphenyl)sulfonyl]amino]phenyl]ethenyl]pyridine 1-oxide, inclusive of their hydrates and their salts.

6. A method for the treatment of mammals suffering from cancer, which comprises administering to the sufferer a therapeutically effective amount of a compound of claim 1 or a pharmaceutically acceptable hydrate or salt thereof.

7. A pharmaceutical composition for the treatment of mammals suffering from cancer, which comprises a therapeutically effective amount of a compound of claim 1 or a pharmaceutically acceptable hydrate or salt thereof in combination with a pharmaceutically effective carrier therefor.

8. The compound of claim 1, wherein $E^-$ comprises an anion selected from the group consisting of halogen ion, chlorate ion, and nitrate ion.

9. The method of claim 6, wherein the mammals are humans.

10. The pharmaceutical composition of claim 9 wherein the mammals are humans.

11. The method of claim 9, wherein the cancer is any one of lung cancer, breast cancer, gastrointestinal cancer, prostrate cancer and blood cancer.

12. The pharmaceutical composition of claim 10, wherein the cancer is any one of lung cancer, breast cancer, gastrointestinal cancer, prostrate cancer and blood cancer.

13. The compound of claim 4 selected from (E)-4-[2-[2-[N-acetyl-N-[(p-methoxyphenyl)sulfonyl]amino]phenyl]ethenyl]pyridine 1-oxide, its hydrates and salts.

14. The method of claim 6 for the treatment of mammals suffering from cancer, which comprises administering to the sufferer a therapeutically effective amount of (E)-4-[2-[2-[N-acetyl-N-[(p-methoxyphenyl)sulfonyl]amino]phenyl]ethenyl]pyridine 1-oxide or a pharmaceutically acceptable hydrate or salt thereof.

15. The pharmaceutical composition of claim 7 for the treatment of mammals suffering from cancer, which comprises a therapeutically effective amount of (E)-4-[2-[2-[N-acetyl-N-[(p-methoxyphenyl)sulfonyl]amino]phenyl]ethenyl]pyridine 1-oxide or a pharmaceutically acceptable hydrate or salt thereof in combination with a pharmaceutically acceptable carrier therefor.

16. The compound of claim 4 selected from (E)-4-[2-[2-[[(p-methoxyphenyl)sulfonyl]amino]phenyl]ethenyl]pyridine, its hydrates and salts.

17. The method of claim 6 for the treatment of mammals suffering from cancer, which comprises administering to the sufferer a therapeutically effective amount of (E)-4-[2-[2-[[(p-methoxyphenyl)sulfonyl]amino]phenyl]ethenyl]pyridine or a pharmaceutically acceptable hydrate or salt thereof.

18. The pharmaceutical composition of claim 8 for the treatment of mammals suffering from cancer, which comprises a therapeutically effective amount of (E)-4-[2-[2-[[(p-methoxyphenyl)sulfonyl]amino]phenyl]ethenyl]pyridine or a pharmaceutically acceptable hydrate or salt thereof in combination with a pharmaceutically effective carrier therefor.

19. The compound of claim 4 selected from (E)-4-[2-[2-[[(p-methoxyphenyl)sulfonyl]amino]phenyl]ethenyl]pyridine 1-oxide, its hydrates and salts.

20. The method of claim 6 for the treatment of mammals suffering from cancer, which comprises administering to the sufferer a therapeutically effective amount of (E)-4-[2-[2-[[(p-methoxyphenyl)sulfonyl]amino]phenyl]ethenyl]pyridine 1-oxide or a pharmaceutically acceptable hydrate or salt thereof.

21. The pharmaceutical composition of claim 7 for the treatment of mammals suffering from cancer, which comprises a therapeutically effective amount of (E)-4-[2-[2-[[(p-methoxyphenyl)sulfonyl]amino]phenyl]ethenyl]pyridine 1-oxide or a pharmaceutically acceptable hydrate or salt thereof in combination with a pharmaceutically effective carrier therefor.

* * * * *